United States Patent
Caplin

(10) Patent No.: US 10,370,707 B2
(45) Date of Patent: Aug. 6, 2019

(54) MULTIPLEX PROBES

(71) Applicant: Fluoresentric, Inc, Park City, UT (US)

(72) Inventor: Brian Caplin, Park City, UT (US)

(73) Assignee: FLUORESENTRIC, INC., Park City, UT (US)

(*) Notice: Subject to any disclaimer, the term of this patent is extended or adjusted under 35 U.S.C. 154(b) by 379 days.

(21) Appl. No.: 14/510,939

(22) Filed: Oct. 9, 2014

(65) Prior Publication Data

US 2015/0099659 A1   Apr. 9, 2015

Related U.S. Application Data

(60) Provisional application No. 61/888,754, filed on Oct. 9, 2013.

(51) Int. Cl.
| | | |
|---|---|---|
| *C12Q 1/68* | (2018.01) | |
| *C07H 21/00* | (2006.01) | |
| *C12Q 1/686* | (2018.01) | |
| *C12Q 1/6818* | (2018.01) | |

(52) U.S. Cl.
CPC .......... *C12Q 1/686* (2013.01); *C12Q 1/6818* (2013.01)

(58) Field of Classification Search
CPC .................... C12Q 1/68; C07H 21/00
See application file for complete search history.

(56) References Cited

U.S. PATENT DOCUMENTS

| | | | |
|---|---|---|---|
| 4,683,195 A | 7/1987 | Mullis et al. | |
| 4,965,188 A | 10/1990 | Mullis et al. | |
| 5,219,727 A | 6/1993 | Wang et al. | |
| 5,314,809 A | 5/1994 | Erlich et al. | |
| 5,476,774 A | 12/1995 | Wang et al. | |
| 5,491,063 A | 2/1996 | Fisher et al. | |
| 5,538,848 A | 7/1996 | Livak et al. | |
| 5,571,673 A | 11/1996 | Picone | |
| 5,573,906 A | 11/1996 | Bannwarth et al. | |
| 5,660,988 A | 8/1997 | Duck et al. | |
| 5,804,375 A | 9/1998 | Gelfand et al. | |
| 6,001,611 A | 12/1999 | Will | |
| 6,033,881 A | 3/2000 | Himmler et al. | |
| 6,040,166 A | 3/2000 | Erlich et al. | |
| 6,197,563 B1 | 3/2001 | Erlich et al. | |
| 6,214,587 B1 | 4/2001 | Dattagupta et al. | |
| 6,506,568 B2 | 1/2003 | Shriver | |
| 6,617,137 B2 | 9/2003 | Dean et al. | |
| 6,692,918 B2 | 2/2004 | Kurn | |
| 6,740,745 B2 | 5/2004 | Auerbach et al. | |
| 6,815,165 B2 | 11/2004 | Lee et al. | |
| 6,821,727 B1* | 11/2004 | Livak .................. | C12Q 1/6818 435/6.1 |
| 6,977,148 B2 | 12/2005 | Dean et al. | |
| 7,074,600 B2 | 7/2006 | Dean et al. | |
| 7,081,226 B1 | 7/2006 | Wittwer et al. | |
| 7,160,998 B2 | 1/2007 | Wittwer et al. | |
| 7,838,235 B2 | 11/2010 | Caplin | |
| 8,119,352 B2 | 2/2012 | Kozma et al. | |
| 8,455,190 B2 | 6/2013 | Makrigiorgos | |
| 9,139,882 B2 | 9/2015 | Caplin | |
| 9,353,408 B2 | 5/2016 | Caplin | |
| 9,670,531 B2 | 6/2017 | Caplin | |
| 2003/0073147 A1 | 4/2003 | Alderete et al. | |
| 2004/0053254 A1 | 3/2004 | Wangh et al. | |
| 2004/0058378 A1 | 3/2004 | Kong et al. | |
| 2004/0248105 A1 | 12/2004 | Kumar | |
| 2004/0259100 A1 | 12/2004 | Gunderson et al. | |
| 2005/0181394 A1 | 8/2005 | Steemers et al. | |
| 2005/0227257 A1* | 10/2005 | Abravaya ............ | C12Q 1/6818 435/6.11 |
| 2005/0233363 A1 | 10/2005 | Harding et al. | |
| 2005/0244835 A1 | 11/2005 | Chou | |
| 2006/0063175 A1 | 3/2006 | Ku et al. | |
| 2006/0147955 A1 | 7/2006 | Allawi et al. | |
| 2007/0020672 A1 | 1/2007 | Wittwer et al. | |
| 2007/0054276 A1 | 3/2007 | Sampson | |
| 2007/0054311 A1 | 3/2007 | Kamberov et al. | |
| 2007/0219122 A1 | 9/2007 | Glazer et al. | |
| 2008/0044812 A1 | 2/2008 | Molly et al. | |
| 2008/0241893 A1 | 10/2008 | Weisburg et al. | |
| 2009/0011408 A1 | 1/2009 | Sorge et al. | |
| 2009/0068641 A1 | 3/2009 | Bergeron et al. | |

(Continued)

FOREIGN PATENT DOCUMENTS

| | | |
|---|---|---|
| EP | 2065465 A2 | 6/2009 |
| EP | 2530466 A1 | 12/2012 |

(Continued)

OTHER PUBLICATIONS

Bannwarth et al., Helvetica Chimica Acta 71 :2085 (1988).*
HIV-1 Sequence (K02007.1) in GENEBANK downloaded Apr. 29, 2018 (Year: 1985).*
Holland et al., PNAS 88:7276 (1991). (Year: 1991).*
Lyamichev et al. Nature Biotechnology 17 :202(1999). (Year: 1999).*
Rudert et al,Biotechniques 22(6) :1140 (Year: 1997).*
Saqnchez-Pescador et al., Science 227 :484 (Year: 1985).*
Bustin S. A., et al., The MIQE Guidelines: Minimum Information for Publication of Quantitative Real-Time PCR Experiments. Clinical Chemistry, 2009, 55(4), 1-12.

(Continued)

*Primary Examiner* — Ethan C Whisenant
(74) *Attorney, Agent, or Firm* — Cooley LLP

(57) ABSTRACT

Methods and reagents suitable for conducing polymerase chain reaction are described. In particular, the disclosure provides probes and primers that are suitable in dynamic flux amplification procedures. In aspects, the disclosure provides long oligonucleotide probes and primers, as well as triplex forming probes and primers, which function within the narrow Tm ranges used with dynamic flux amplification. However, embodiments are also provided wherein the probes and primers taught herein can be utilized in standard PCR.

15 Claims, 24 Drawing Sheets

Specification includes a Sequence Listing.

(56) References Cited

U.S. PATENT DOCUMENTS

| | | | |
|---|---|---|---|
| 2009/0075269 A1* | 3/2009 | Caplin | C12Q 1/6827 435/6.18 |
| 2009/0226881 A1 | 9/2009 | Godfrey et al. | |
| 2009/0325156 A1* | 12/2009 | Figg | C12Q 1/6883 435/6.11 |
| 2011/0097764 A1 | 4/2011 | Johnson et al. | |
| 2011/0143357 A1 | 6/2011 | Caplin | |
| 2014/0274756 A1 | 9/2014 | Nguyen et al. | |
| 2015/0376689 A1 | 12/2015 | Caplin | |
| 2016/0230218 A1 | 8/2016 | Caplin | |
| 2017/0198342 A1 | 7/2017 | Caplin | |
| 2017/0226576 A1 | 8/2017 | Caplin | |

FOREIGN PATENT DOCUMENTS

| | | |
|---|---|---|
| RU | 2186112 C2 | 7/2002 |
| RU | 2251552 C2 | 5/2005 |
| RU | 2427648 C1 | 8/2011 |
| RU | 2451086 C1 | 5/2012 |
| WO | WO 1998/045474 A1 | 10/1998 |
| WO | WO 2000/043545 A2 | 7/2000 |
| WO | WO 2006/074334 A2 | 7/2006 |
| WO | WO 2008/119081 A1 | 10/2008 |
| WO | WO 2010/013017 A1 | 2/2010 |
| WO | WO 2011/030145 A1 | 3/2011 |
| WO | WO 2011/053987 A1 | 5/2011 |
| WO | WO 2012/095639 A2 | 7/2012 |
| WO | WO 2012/096430 A1 | 7/2012 |
| WO | WO 2012/145725 A2 | 10/2012 |
| WO | WO 2013/113748 A1 | 8/2013 |
| WO | WO 2015/054516 A2 | 4/2015 |
| WO | WO 2016/007914 A1 | 1/2016 |

OTHER PUBLICATIONS

Breslauer et al., Predicting DNA duplex stability from the base sequence, Proc Natl Academy Science, 1986, 83:3746-3750.

Rychlik et al., A computer program for choosing optimal oligonucleotides for filter hybridization, sequencing and in vitro amplification of DNA, Nucleic Acids Res., 1989, 17:8543-8551.

Definition of Minimum Performance Requirements for Analytical Methods of GMO Testing, European Network of GMO Laboratories, Oct. 2008.

International Search Report in PCT/US2014/059935 dated Mar. 20, 2015 (5 pages).

Written Opinion in PCT/US2014/059935 dated Mar. 20, 2015 (7 pages).

Sambrook, et al., Molecular cloning—A Laboratory Manual, 1985, Cold Springs Harbor, N.Y.

Supplementary European Sarch Report, EP Appl. No. 14852079.4, 8 pages (dated May 23, 2017).

Allawi, Hatim T., and SantaLucia, Jr., John. "Thermodynamics and NMR of Internal G♦T Mismatches in DNA." Biochemistry (1997); 36.34: 10581-10594.

Anonymous: "Performing Fast PCR Using Bio-Rad Thermal Cyclers", Jan. 1, 2005 (Jan. 1, 2005), XP55402836, Retrieved from the Internet: URL:http://www.bio-rad.com/LifeScience/jobs/2005/05-0739/fast_pcr.pdf [retrieved on Aug. 31, 2017], 21 pages.

Arya et al. "Basic principles of real-time quantitative PCR," Expert Review of Molecular Diagnostics (2005); vol. 5, No. 2, pp. 209-219.

Auer, Tatiana et al., "Selective amplification of RNA utilizing the nucleotide analog dITP and Thermus thermophilus DNA polymerase", Nucleic Acids Research, 1996, pp. 5021-5025, vol. 24, No. 24.

Definition of Minimum Performance Requirements for Analytical Methods of GMO Testing, European Network of GMO Laboratories, Oct. 2008, 8 pages.

European Extended Search Report, European Application No. 12187764. 1, dated Mar. 1, 2013, 7 pages.

Extended European Search Report in Application No. 16161557.0, dated Oct. 10, 2016, 6 pages.

Hymas et al., "Use of lyophilized standards for the calibration of a newly developed real time PCR assay for human herpes type six (HHV6) variants A and B," J. Virol. Meth., 2005, vol. 128, pp. 143-150.

International Preliminary Report on Patentability for International Application No. PCT/US2008/058786, dated Sep. 29, 2009, 6 pages.

International Preliminary Report on Patentability for International Application No. PCT/US2015/040035, dated Jan. 10, 2017, 16 pages.

International Preliminary Report on Patentability for International Application No. PCT/US2014/059935 dated Apr. 12, 2016, 8 pages.

International Search Report and Written Opinion for International Application No. PCT/US2016/052335, dated Aug. 29, 2008, 11 pages.

International Search Report and Written Opinion for International Application No. PCT/US2008/058786, dated Aug. 29, 2008, 8 pages.

International Search Report and Written Opinion for International Application No. PCT/US2015/040035, dated Oct. 30, 2015, 18 pages.

Lowe, Todd, et al. "A computer program for selection of oligonucleotide primers for polymerase chain reactions." Nucleic Acids Research (1990); 18.7: 1757-1761.

Masny, A. et al., "Ligation Mediated PCR Performed at Low Denaturation Temperatures-PCT Melting Profiles," Nucleic Acids Research, Sep. 15, 2003, pp. 1-6, vol. 31, No. 18.

Neo, Jia Ling, and Uttamchandani, Mahesh. "Visual DNA Detection and SNP Genotyping Using Asymmetric PCR and Split DNA Enzymes." Nucleic Acid Detection: Methods and Protocols (2013): 141-151.

Notomi, T. et al., "Loop-Mediated Isothermal Amplification of DNA," Nucleic Acids Research, Jan. 2000, pp. 1-7, vol. 28, No. 12.

Partial Supplementary European Search Report for Application No. EP 15818265.9 dated Feb. 7, 2018, 16 pages.

Rychlik, Wojciech, and Rhoads, Robert E. "A computer program for choosing optimal oligonudeotides for filter hybridization, sequencing and in vitro amplification of DNA." Nucleic Acids Research (1989); 17.21:8543-8551.

Santalucia, Jr., John. "A unified view of polymer, dumbbell, and oligonucleotide DNA nearest-neighbor thermodynamics." Proceedings of the National Academy of Sciences (1998); 95.4: 1460-1465.

Sullivan, D., et al., "Fast PCR: General Considerations for Minimizing Run Times and Maximizing Throughput." Mar. 7, 2007 (Mar. 7, 2007), XP55402819, Retrieved from the Internet: URL:http://www.bio-rad.com/webroot/web/pdf/lsr/literature/Bulletin_5362. pdf [retrieved on Aug. 31, 2017], 6 pages.

* cited by examiner

FIGURE 12
 Quenched
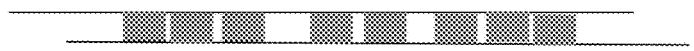 Quenched
 Ex494 Em650

FIGURE 20
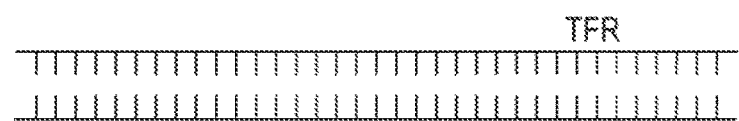
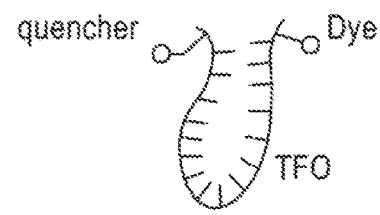
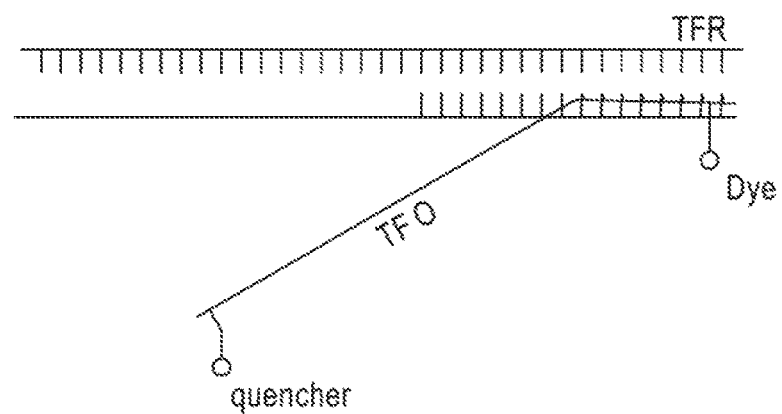

6-9 bp

SEQUENCE LISTING

```
<160> NUMBER OF SEQ ID NOS: 78

<210> SEQ ID NO 1
<211> LENGTH: 72
<212> TYPE: DNA
<213> ORGANISM: Artificial Sequence
<220> FEATURE:
<223> OTHER INFORMATION: Folded hairpin-like probe example

<400> SEQUENCE: 1
acctccaatg ccaaacatta ctccttgact caatgtttcc tgtgccagca tgcgcttatt     60
agacccatgg cc                                                         72

<210> SEQ ID NO 2
<211> LENGTH: 67
<212> TYPE: DNA
<213> ORGANISM: Artificial Sequence
<220> FEATURE:
<223> OTHER INFORMATION: Folded hairpin-like probe example

<400> SEQUENCE: 2
agcacgcagt tattctgctg gtgcacttgc cacttgcatg ggcctcatat acaacaggat     60
gggggct                                                               67

<210> SEQ ID NO 3
<211> LENGTH: 83
<212> TYPE: DNA
<213> ORGANISM: Artificial Sequence
<220> FEATURE:
<223> OTHER INFORMATION: Folded hairpin-like probe example

<400> SEQUENCE: 3
atggacgtgg cttagcgtat atttatgctg atggaaaaat ggtaaacgaa gctttagttc     60
gtcaaggctt ggctaaagtt gct                                             83

<210> SEQ ID NO 4
<211> LENGTH: 83
<212> TYPE: DNA
<213> ORGANISM: Artificial Sequence
<220> FEATURE:
<223> OTHER INFORMATION: Folded hairpin-like probe example

<400> SEQUENCE: 4
```
atggacgtgg cttagcgtat atttatgctg atggaaaaat ggtaaacgaa gctttagttc    60
gtcaaggctt ggctaaagtt gct                                            83

<210> SEQ ID NO 5
<211> LENGTH: 67
<212> TYPE: DNA
<213> ORGANISM: Artificial Sequence
<220> FEATURE:
<223> OTHER INFORMATION: Folded hairpin-like probe example

<400> SEQUENCE: 5
agcactcagt tattctgctg gtgcacttgc cagttgcatg ggcctcatat acaacaggat    60
gggggct                                                              67

<210> SEQ ID NO 6
<211> LENGTH: 38
<212> TYPE: DNA
<213> ORGANISM: Artificial Sequence
<220> FEATURE:
<223> OTHER INFORMATION: Folded hairpin-like probe example

<400> SEQUENCE: 6
tggcaatccc aggttttctt ttctacctgt ttgctcaa                            38

<210> SEQ ID NO 7
<211> LENGTH: 36
<212> TYPE: DNA
<213> ORGANISM: Artificial Sequence
<220> FEATURE:
<223> OTHER INFORMATION: Folded hairpin-like probe example

<400> SEQUENCE: 7
cagacccatc ccccaggtga gggactatgg cctcct                              36

<210> SEQ ID NO 8
<211> LENGTH: 30
<212> TYPE: DNA
<213> ORGANISM: Artificial Sequence
<220> FEATURE:
<223> OTHER INFORMATION: Folded hairpin-like probe example

<400> SEQUENCE: 8
tcaatggctg aggtgaggta ccccgcaggg                                     30

<210> SEQ ID NO 9
<211> LENGTH: 42
<212> TYPE: DNA
<213> ORGANISM: Artificial Sequence
<220> FEATURE:
<223> OTHER INFORMATION: Folded hairpin-like probe example

<400> SEQUENCE: 9
tttgctctga gagttccccc tgtcccctcc accttccctc ag                       42

<210> SEQ ID NO 10
<211> LENGTH: 45
<212> TYPE: DNA
<213> ORGANISM: Artificial Sequence
<220> FEATURE:
<223> OTHER INFORMATION: Folded hairpin-like probe example

<400> SEQUENCE: 10
tgcaagagtc accaaaattg ccgagaggcc ccagttagca tccca                    45

<210> SEQ ID NO 11
<211> LENGTH: 47
<212> TYPE: DNA
<213> ORGANISM: Artificial Sequence
<220> FEATURE:
<223> OTHER INFORMATION: Made in lab

<400> SEQUENCE: 11
gatcgatgct agctatggcc cctcagagcc ggctctgagg ggccata        47

<210> SEQ ID NO 12
<211> LENGTH: 180
<212> TYPE: DNA
<213> ORGANISM: Ebola virus

<400> SEQUENCE: 12
acatttcggc aaaggatttg agaaacatta tgtatgatca cttgcctggt tttggaactg        60
ctttccacca attagtacaa gtgatttgta aattgggaaa agatagcaac tcattggaca       120
tcattcatgc tgagttccag gccagcctgg ctgaaggaga ctctcctcaa tgtgccctaa       180

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
atcacttgcc tggttttgga actgctttcc acc        33

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
ccttcagcca ggctggcctg gaact        25

<210> SEQ ID NO 15
<211> LENGTH: 54
<212> TYPE: DNA
<213> ORGANISM: Artificial Sequence
<220> FEATURE:
<223> OTHER INFORMATION: Oligonucleotide probe targeting ebola virus DNA

<400> SEQUENCE: 15
tacaagtgat ttgtaaattg ggaaagatag caactcattg gacatcattc atgc        54

<210> SEQ ID NO 16
<211> LENGTH: 294
<212> TYPE: DNA
<213> ORGANISM: bacteriophage SPW

<400> SEQUENCE: 16
ccattgccat atttggttat caggtatctg ttagagggc taaagctaac ccaccaattc        60
ctgtgccaga gsaataaaat tcccatcgca attcctctgt gagcactgaa atagggcggt       120
gcatgaacaa tagccggtag gtatgtcaga aaacctccaa tgccaaacat tactccttga       180
ctcaatgttt cctgtgccca cgatgcgctt attagaccca tggccatcaa aagtgacccg       240
agcaccatcg tttgttggat tgaaaagaag tgctgtagta cgttattacc gatg             294

<210> SEQ ID NO 17
<211> LENGTH: 63
<212> TYPE: DNA
<213> ORGANISM: Artificial Sequence
<220> FEATURE:
<223> OTHER INFORMATION: Primer

<400> SEQUENCE: 17
attgccatcc atatttggtt atcaggtatc tcgttagagg ggctaaagct aacccaccat        60
tcc        63

<210> SEQ ID NO 18
<211> LENGTH: 57
<212> TYPE: DNA
<213> ORGANISM: Artificial Sequence
<220> FEATURE:
<223> OTHER INFORMATION: primer

<400> SEQUENCE: 18
ggtaataacg tactacatca gcacttcttt tcaatccaac gatggtgctg ggtcact        57

<210> SEQ ID NO 19
<211> LENGTH: 73
<212> TYPE: DNA
<213> ORGANISM: Artificial Sequence
<220> FEATURE:
<223> OTHER INFORMATION: Oligonucleotide probe - targets bacteriophage
      SPW

<400> SEQUENCE: 19
acctccaatg ccaaacatta ctccttgact caatgtttcc tgtgcccacg atgcgcttat        60
tagacccatg gcc        73

<210> SEQ ID NO 20
<211> LENGTH: 365
<212> TYPE: DNA
<213> ORGANISM: Influenza A virus
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t

<400> SEQUENCE: 20
gagtgagcga ggactgcagc gtagacgctt tgtccaaaat gccctnaatg ggaatgggga        60
tccaataaca tggacagagc agttaaactg tataggaagc ttaagggata acgttccatg       120
gggccaaaga aatagcactc agttattvtg ctggtgcact tgccagttgc atgggcctca       180

```
tatacaacag gatgggggct gtgaccacng aagcngcatt ggcctngtat gtgcaacntg      240
tgaacagatt gctgactccc agcataggtc tcataggcaa tggtnacaac aaccaatcca      300
ttaataagac atgagaacag aatggttctg ccagcacta cagctaaggc tatggagcaa      360
atggc                                                                 365
```

```
<210> SEQ ID NO 21
<211> LENGTH: 41
<212> TYPE: DNA
<213> ORGANISM: Influenza A virus

<400> SEQUENCE: 21
gtgagcgagg actgcagcgt agacgctttg tccaaaatgc c                         41

<210> SEQ ID NO 22
<211> LENGTH: 66
<212> TYPE: DNA
<213> ORGANISM: Influenza A virus

<400> SEQUENCE: 22
gccatttgct ccatagcctt agctgtagtg ctggccagaa ccattctgtt ctcatgtctt      60
attaat                                                                66

<210> SEQ ID NO 23
<211> LENGTH: 67
<212> TYPE: DNA
<213> ORGANISM: Artificial Sequence
<220> FEATURE:
<223> OTHER INFORMATION: Oligonucleotide probe - targets Flu mat A
      sequence

<400> SEQUENCE: 23
agcactcagt tattctgctg gtgcacttgc cagttgcatg ggcctcatat acaacaggat      60
gggggct                                                               67

<210> SEQ ID NO 24
<211> LENGTH: 254
<212> TYPE: DNA
<213> ORGANISM: Staphylococcus aureus

<400> SEQUENCE: 24
agcaagtgca tttacgaaaa aaatggtaga aaatgcaaag aaaattgaag tcgagtttga      60
caaaggccaa agaactgata aatatggacg tggcttagcg tatatttatg ctgatggaaa     120
aatggtaaac gaagctttag ttcgtcaagg cttggctaaa gttgcttatg tttataaacc     180
taacaataca catgaacaac ttttaagaaa aagtgaagca caagcgaaaa aagagaaatt     240
aaatatttgg agcg                                                      254

<210> SEQ ID NO 25
<211> LENGTH: 56
<212> TYPE: DNA
<213> ORGANISM: Staphylococcus aureus

<400> SEQUENCE: 25
agcaagtgca tttacgaaaa aaatggtaga aaatgcaaag aaaattgaag tcgagt         56

<210> SEQ ID NO 26
<211> LENGTH: 77
<212> TYPE: DNA
<213> ORGANISM: Staphylococcus aureus
```

<400> SEQUENCE: 26
cgctccaaat atttaatttc tcttttttg cttgtgcttc acttttctt aaaagttgtt    60 catgtgtatt gttaggt    77

<210> SEQ ID NO 27
<211> LENGTH: 83
<212> TYPE: DNA
<213> ORGANISM: Artificial Sequence
<220> FEATURE:
<223> OTHER INFORMATION: Oligonucleotide probe - targets Staphylococcus
      aureus

<400> SEQUENCE: 27
atggacgtgg cttagcgtat atttatgctg atggaaaaat ggtaaacgaa gctttagttc    60
gtcaaggctt ggctaaagtt gct    83

<210> SEQ ID NO 28
<211> LENGTH: 67
<212> TYPE: DNA
<213> ORGANISM: Artificial Sequence
<220> FEATURE:
<223> OTHER INFORMATION: Oligonucleotide probe - targets Staphylococcus
      aureus

<400> SEQUENCE: 28
agcactcagt tattctgctg gtgcacttgc cagttgcatg ggcctcatat acaacaggat    60
gggggct    67

<210> SEQ ID NO 29
<211> LENGTH: 48
<212> TYPE: DNA
<213> ORGANISM: Artificial Sequence
<220> FEATURE:
<223> OTHER INFORMATION: Made in lab - primer

<400> SEQUENCE: 29
agggcggtgc atgaacaata gccggtaggt atgtcagaaa acctccaa    48

<210> SEQ ID NO 30
<211> LENGTH: 39
<212> TYPE: DNA
<213> ORGANISM: Artificial Sequence
<220> FEATURE:
<223> OTHER INFORMATION: Made in lab - primer

<400> SEQUENCE: 30
atggccatgg gtctaataag cgcatcgtgg gcacaggaa    39

<210> SEQ ID NO 31
<211> LENGTH: 180
<212> TYPE: DNA
<213> ORGANISM: Artificial Sequence
<220> FEATURE:
<223> OTHER INFORMATION: Made in lab - target sequence

<400> SEQUENCE: 31
aagagggaag aggggagggg cggtgcatga acaatagccg gtaggtatgt cagaaaacct    60
ccaatgccaa acattactcc ttgactcaat gtttcctgtg cccacgatgc gcttattaga   120
cccatggcca tcaaaagtga cccgagcacc atcgtttgtt ggattgaaaa gaagtgctgt   180

<210> SEQ ID NO 32

```
<211> LENGTH: 31
<212> TYPE: DNA
<213> ORGANISM: Artificial Sequence
<220> FEATURE:
<223> OTHER INFORMATION: Triplex forming region sequence
<220> FEATURE:
<221> NAME/KEY: misc_feature
<222> LOCATION: (18)..(18)
<223> OTHER INFORMATION: n is a, c, g, or t

<400> SEQUENCE: 32
gtgtgggaag aggggganga gggggaggag c                              31

<210> SEQ ID NO 33
<211> LENGTH: 30
<212> TYPE: DNA
<213> ORGANISM: Artificial Sequence
<220> FEATURE:
<223> OTHER INFORMATION: Triplex forming region sequence
<220> FEATURE:
<221> NAME/KEY: misc_feature
<222> LOCATION: (14)..(14)
<223> OTHER INFORMATION: n is a, c, g, or t

<400> SEQUENCE: 33
gctgcctccc ctcntccctc ttccccacac                                30

<210> SEQ ID NO 34
<211> LENGTH: 31
<212> TYPE: DNA
<213> ORGANISM: Artificial Sequence
<220> FEATURE:
<223> OTHER INFORMATION: Triplex forming region sequence
<220> FEATURE:
<221> NAME/KEY: misc_feature
<222> LOCATION: (18)..(18)
<223> OTHER INFORMATION: n is a, c, g, or t

<400> SEQUENCE: 34
gtgtgggaag aggggganga gggggaggag c                              31

<210> SEQ ID NO 35
<211> LENGTH: 30
<212> TYPE: DNA
<213> ORGANISM: Artificial Sequence
<220> FEATURE:
<223> OTHER INFORMATION: Triplex forming region sequence
<220> FEATURE:
<221> NAME/KEY: misc_feature
<222> LOCATION: (14)..(14)
<223> OTHER INFORMATION: n is a, c, g, or t

<400> SEQUENCE: 35
gctgcctccc ctcntccctc ttccccacac                                30

<210> SEQ ID NO 36
<211> LENGTH: 22
<212> TYPE: DNA
<213> ORGANISM: Artificial Sequence
<220> FEATURE:
<223> OTHER INFORMATION: Triplex forming sequence

<400> SEQUENCE: 36 ggaggggggag aagggagaag gg                                       22

<210> SEQ ID NO 37
<211> LENGTH: 22
<212> TYPE: DNA
<213> ORGANISM: Artificial Sequence
```

```
<220> FEATURE:
<223> OTHER INFORMATION: Triplex forming sequence

<400> SEQUENCE: 37
cccttctccc ttctcccct cc                                              22

<210> SEQ ID NO 38
<211> LENGTH: 22
<212> TYPE: DNA
<213> ORGANISM: Artificial Sequence
<220> FEATURE:
<223> OTHER INFORMATION: Triplex forming sequence

<400> SEQUENCE: 38 ggtggggtg ttgggtgttg gg                                              22

<210> SEQ ID NO 39
<211> LENGTH: 22
<212> TYPE: DNA
<213> ORGANISM: Artificial Sequence
<220> FEATURE:
<223> OTHER INFORMATION: Triplex forming sequence

<400> SEQUENCE: 39 ggtggggtg ttgggtgttg gg                                              22

<210> SEQ ID NO 40
<211> LENGTH: 31
<212> TYPE: DNA
<213> ORGANISM: Artificial Sequence
<220> FEATURE:
<223> OTHER INFORMATION: Triplex forming sequence
<220> FEATURE:
<221> NAME/KEY: misc_feature
<222> LOCATION: (18)..(18)
<223> OTHER INFORMATION: n is a, c, g, or t

<400> SEQUENCE: 40
gtgtgggaag aggggganga gggggaggag c                                   31

<210> SEQ ID NO 41
<211> LENGTH: 30
<212> TYPE: DNA
<213> ORGANISM: Artificial Sequence
<220> FEATURE:
<223> OTHER INFORMATION: Triplex forming sequence
<220> FEATURE:
<221> NAME/KEY: misc_feature
<222> LOCATION: (13)..(13)
<223> OTHER INFORMATION: n is a, c, g, or t

<400> SEQUENCE: 41
gctgcctccc ctnctccctc ttccccacac                                     30

<210> SEQ ID NO 42
<211> LENGTH: 13
<212> TYPE: DNA
<213> ORGANISM: Unknown
<220> FEATURE:
<223> OTHER INFORMATION: Naturally occurring TFR sequence in double
      stranded DNA

<400> SEQUENCE: 42 tttttcccg tcc                                                        13

<210> SEQ ID NO 43
<211> LENGTH: 12
```

```
<212> TYPE: DNA
<213> ORGANISM: Unknown
<220> FEATURE:
<223> OTHER INFORMATION: Naturally occurring TFR sequence in double
      stranded DNA

<400> SEQUENCE: 43
ggacgggaaa aa                                                         12

<210> SEQ ID NO 44
<211> LENGTH: 17
<212> TYPE: DNA
<213> ORGANISM: Spirometra erinaceieuropaei

<400> SEQUENCE: 44
ggcgaggggg gagcggg                                                    17

<210> SEQ ID NO 45
<211> LENGTH: 17
<212> TYPE: DNA
<213> ORGANISM: Toxocara canis

<400> SEQUENCE: 45
cccgctcccc cctcgcc                                                    17

<210> SEQ ID NO 46
<211> LENGTH: 13
<212> TYPE: DNA
<213> ORGANISM: Unknown
<220> FEATURE:
<223> OTHER INFORMATION: Naturally occurring TFR sequence in double
      stranded DNA

<400> SEQUENCE: 46
ggaggtgggg gag                                                        13

<210> SEQ ID NO 47
<211> LENGTH: 13
<212> TYPE: DNA
<213> ORGANISM: Unknown
<220> FEATURE:
<223> OTHER INFORMATION: Naturally occurring TFR sequence in double
      stranded DNA

<400> SEQUENCE: 47
ctcccccacc tcc                                                        13

<210> SEQ ID NO 48
<211> LENGTH: 13
<212> TYPE: DNA
<213> ORGANISM: Unknown
<220> FEATURE:
<223> OTHER INFORMATION: Naturally occurring TFR sequence in double
      stranded DNA

<400> SEQUENCE: 48
ggaggtgggg gag                                                        13

<210> SEQ ID NO 49
<211> LENGTH: 14
<212> TYPE: DNA
<213> ORGANISM: Unknown
<220> FEATURE:
<223> OTHER INFORMATION: Naturally occurring TFR sequence in double
      stranded DNA

<400> SEQUENCE: 49
```
ctccccccac ctcc                                                         14

<210> SEQ ID NO 50
<211> LENGTH: 27
<212> TYPE: DNA
<213> ORGANISM: Human adenovirus D strain

<400> SEQUENCE: 50
cgtgagctcg tcttccagga gcctgat                                           27

<210> SEQ ID NO 51
<211> LENGTH: 20
<212> TYPE: DNA
<213> ORGANISM: Human adenovirus D strain

<400> SEQUENCE: 51
gtctcccggt gcgtcgccgt                                                   20

<210> SEQ ID NO 52
<211> LENGTH: 480
<212> TYPE: DNA
<213> ORGANISM: Human adenovirus D strain

<400> SEQUENCE: 52
ctgggcattg cgggccgaga ccgtgagctc gtcttccagg agcctgatga gctcggcgat       60
gacccgtaac gcccggctct ggcactcgag cagaaggtcc tcggactact cgagccgcta      120
ggtggcgcgc acctcgcgct cgaaatcccc gggggcctcc tcttcttcct cttcttccat      180
ccaccgcgcg tggagcgcga gctttagggg cccccggagg agaagaagga gaagaaggta      240
gacgacctct tcttctattt cttcctctgg gggcggtggt ggtggcgggg cccgacgacg      300
ctgctggaga agaagataaa gaaggagacc cccgccacca ccaccgcccc gggctgctgc      360
acggcgacgc accgggagac ggtcgacgaa gcgctcgatc atctcccgc ggcggcgacg       420 tgccgctgcg tggccctctg ccagctgctt cgcgagctag tagaggggcg ccgccgctgc      480

<210> SEQ ID NO 53
<211> LENGTH: 25
<212> TYPE: DNA
<213> ORGANISM: Artificial Sequence
<220> FEATURE:
<223> OTHER INFORMATION: Probe targeting adenoviridae DNA

<400> SEQUENCE: 53
ggaggagaag gagaagaaga aggta                                             25

<210> SEQ ID NO 54
<211> LENGTH: 33
<212> TYPE: DNA
<213> ORGANISM: Artificial Sequence
<220> FEATURE:
<223> OTHER INFORMATION: Probe targeting adenoviridae DNA

<400> SEQUENCE: 54
ttttaggagg agaaggagaa gaagaaggta aaa                                    33

<210> SEQ ID NO 55
<211> LENGTH: 25
<212> TYPE: DNA
<213> ORGANISM: Artificial Sequence
<220> FEATURE:
<223> OTHER INFORMATION: Probe targeting adenoviridae DNA

<400> SEQUENCE: 55
ggaggagaag gagaagaaga aggta                                          25

<210> SEQ ID NO 56
<211> LENGTH: 25
<212> TYPE: DNA
<213> ORGANISM: Artificial Sequence
<220> FEATURE:
<223> OTHER INFORMATION: Probe targeting adenoviridae DNA

<400> SEQUENCE: 56
ggaggagaag gagaagaaga aggta                                          25

<210> SEQ ID NO 57
<211> LENGTH: 25
<212> TYPE: DNA
<213> ORGANISM: Artificial Sequence
<220> FEATURE:
<223> OTHER INFORMATION: Probe targeting adenoviridae DNA

<400> SEQUENCE: 57
ggaggagaag gaggagaaga aggta                                          25

<210> SEQ ID NO 58
<211> LENGTH: 25
<212> TYPE: DNA
<213> ORGANISM: Artificial Sequence
<220> FEATURE:
<223> OTHER INFORMATION: Probe targeting adenoviridae DNA

<400> SEQUENCE: 58
ggaggagaag gagaagaaga aggta                                          25

<210> SEQ ID NO 59
<211> LENGTH: 25
<212> TYPE: DNA
<213> ORGANISM: Artificial Sequence
<220> FEATURE:
<223> OTHER INFORMATION: Probe targeting adenoviridae DNA

<400> SEQUENCE: 59
ggaggagaag gagaagaaga aggta                                          25

<210> SEQ ID NO 60
<211> LENGTH: 23
<212> TYPE: DNA
<213> ORGANISM: Artificial Sequence
<220> FEATURE:
<223> OTHER INFORMATION: Probe targeting adenoviridae DNA

<400> SEQUENCE: 60
ggagaagaag ataaagaagg aga                                            23

<210> SEQ ID NO 61
<211> LENGTH: 180
<212> TYPE: DNA
<213> ORGANISM: Ebola virus

<400> SEQUENCE: 61
tgtaaagccg tttcctaaac tctttgtaat acatactagt gaacggacca aaaccttgac    60
gaaaggtggt taatcatgtt cactaaacat ttaacccttt tctatcgttg agtaacctgt   120
agtaagtacg actcaaggtc cggtcggacc gacttcctct gagaggagtt acacgggatt   180

```
<210> SEQ ID NO 62
<211> LENGTH: 47
<212> TYPE: DNA
<213> ORGANISM: Artificial Sequence
<220> FEATURE:
<223> OTHER INFORMATION: Primer

<400> SEQUENCE: 62
gcacataagt tgataattag tgagttgggt gatacataca caagggt          47

<210> SEQ ID NO 63
<211> LENGTH: 47
<212> TYPE: DNA
<213> ORGANISM: Homo sapies

<400> SEQUENCE: 63
cgtgtattca actattaatc actcaaccca ctatgtatgt gttccca          47

<210> SEQ ID NO 64
<211> LENGTH: 39
<212> TYPE: DNA
<213> ORGANISM: Artificial Sequence
<220> FEATURE:
<223> OTHER INFORMATION: Primer

<400> SEQUENCE: 64
ggttgaagaa gttgaggaag aggttgaaga agtgctgag                   39

<210> SEQ ID NO 65
<211> LENGTH: 39
<212> TYPE: DNA
<213> ORGANISM: Homo sapiens

<400> SEQUENCE: 65
ccaacttctt caactccttc tccaacttct tcacgactc                   39

<210> SEQ ID NO 66
<211> LENGTH: 33
<212> TYPE: DNA
<213> ORGANISM: Artificial Sequence
<220> FEATURE:
<223> OTHER INFORMATION: Primer

<400> SEQUENCE: 66
agaaatctcg tgcccaaacc tggtgatgga tcc                         33

<210> SEQ ID NO 67
<211> LENGTH: 33
<212> TYPE: DNA
<213> ORGANISM: Homo sapiens

<400> SEQUENCE: 67
tctttagagc acgggtttgg accactacct agg                         33

<210> SEQ ID NO 68
<211> LENGTH: 33
<212> TYPE: DNA
<213> ORGANISM: Artificial Sequence
<220> FEATURE:
<223> OTHER INFORMATION: Primer

<400> SEQUENCE: 68
agaaatctcg tgcccaaacc tggtgatgaa tcc                         33

<210> SEQ ID NO 69
```

```
<211> LENGTH: 33
<212> TYPE: DNA
<213> ORGANISM: Homo sapiens

<400> SEQUENCE: 69
tctttagagc acgggtttgg accactactt agg                                      33

<210> SEQ ID NO 70
<211> LENGTH: 41
<212> TYPE: DNA
<213> ORGANISM: Artificial Sequence
<220> FEATURE:
<223> OTHER INFORMATION: Primer

<400> SEQUENCE: 70
atgtaaggaa gtccaaatgt tcacctgaag acaactgtgg t                             41

<210> SEQ ID NO 71
<211> LENGTH: 41
<212> TYPE: DNA
<213> ORGANISM: Homo sapiens

<400> SEQUENCE: 71
tacattcctt caggtttaca agtggacttc tgttgacacc a                             41

<210> SEQ ID NO 72
<211> LENGTH: 28
<212> TYPE: DNA
<213> ORGANISM: Artificial Sequence
<220> FEATURE:
<223> OTHER INFORMATION: Primer

<400> SEQUENCE: 72
gcctctggca acagtaaagc aggggcat                                            28

<210> SEQ ID NO 73
<211> LENGTH: 28
<212> TYPE: DNA
<213> ORGANISM: Homo sapiens

<400> SEQUENCE: 73
cggagaccgt tgtcatttcg tccccgta                                            28

<210> SEQ ID NO 74
<211> LENGTH: 38
<212> TYPE: DNA
<213> ORGANISM: Artificial Sequence
<220> FEATURE:
<223> OTHER INFORMATION: Primer

<400> SEQUENCE: 74
tggcaatccc aggttctctt ttctacctgt ttgctcaa                                 38

<210> SEQ ID NO 75
<211> LENGTH: 38
<212> TYPE: DNA
<213> ORGANISM: Homo sapiens

<400> SEQUENCE: 75
accgttaggg tccaagagaa aagatggaca aacgagtt                                 38

<210> SEQ ID NO 76
<211> LENGTH: 37
<212> TYPE: DNA
<213> ORGANISM: Artificial Sequence
```

```
<220> FEATURE:
<223> OTHER INFORMATION: Primer

<400> SEQUENCE: 76
tggcaatccc aggttttctt ttctacctgt ttgtcaa                              37

<210> SEQ ID NO 77
<211> LENGTH: 37
<212> TYPE: DNA
<213> ORGANISM: Homo sapiens

<400> SEQUENCE: 77
accgttaggg tccaaaagaa aagatggaca aacagtt                              37

<210> SEQ ID NO 78
<211> LENGTH: 30
<212> TYPE: DNA
<213> ORGANISM: Streptococcus dysgalactiae

<400> SEQUENCE: 78
ggagaaggtg aggaagaaga agaggaagaa                                      30
```

MULTIPLEX PROBES

CROSS REFERENCE TO RELATED APPLICATIONS

The present application claims priority to U.S. Provisional Application No. 61/888,754, filed on Oct. 9, 2013, the entire contents of which are hereby incorporated by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FLUO_001_00US_ST25.txt. The text file is 19 KB, was created on Oct. 9, 2014, and is being submitted electronically via EFS-Web.

FIELD

The present disclosure concerns methods and materials useful for conducting PCR amplification protocols.

In particular, the present disclosure describes methods and materials—including probe and primer combinations—that can be utilized in conducting Dynamic Flux Amplification ("DFA").

BACKGROUND

Real-time PCR typically relies on the use of fluorescent molecules that allow quantification or detection of a PCR product in real time, while other detection/quantification chemistries such as electrochemistry are also applicable.

Fluorescent molecules can be DNA binding dyes such as SYBR® Green or fluorescently labeled primers or probes. There are many fluorescent dyes and probe designs available for different applications. The most commonly used DNA-binding dye for real-time PCR is SYBR® Green 1, which binds preferentially to double-stranded DNA (dsDNA) versus single stranded DNA. SYBR Green I fluorescence increases up to 1,000-fold when it binds to dsDNA. Therefore, fluorescence signal is proportional to the amount of dsDNA present.

The major drawback of DNA-binding dyes is their lack of specificity, that is, DNA-binding dyes bind to any dsDNA. As a result, the presence of any nonspecific products in a real-time or endpoint PCR reaction will contribute to the overall fluorescence and affect the accuracy of quantification or detection. Furthermore, DNA-binding dyes cannot be used for quantification or detection in multiplex reactions because fluorescence signals from different products cannot be distinguished without the inclusion of a post PCR melting curve analysis to distinguish the formation of different products.

In contrast, primer-based and probe-based detection chemistries ensure that signal is generated only when the product of interest is amplified. The primer or target-specific oligonucleotide probe is typically labeled with a reporter fluorophore, but in most cases, fluorescence is quenched when the specific target is not yet amplified or when not present in the sample. Usually this is accomplished by attaching a quencher molecule to the primer or probe, and devising some mechanism by which the reporter and quencher are separated when the primer or probe binds to its specific target.

The principal primer/probe detection chemistries in use today are as follows:

Hydrolysis (TaqMan) Probe

Hydrolysis assays include a sequence-specific, fluorescently labeled oligonucleotide probe, in addition to the sequence-specific primers. Hydrolysis assays exploit the 5' exonuclease activity of certain thermostable polymerases, such as Taq or Tth. The hydrolysis probe is labeled with a fluorescent reporter at one end and a quencher at the opposite end, though several variations on this particular design are in common usage. When the probe is intact, fluorscence is quenched due to fluorophore proximity to the quencher. A commonly used fluorescent reporter—quencher pair is fluorescein (FAM), which emits green fluorescence, and Black Hole Quencher 1 dye, although this is just one of many dye/quencher combinations in use.

The amplification reaction includes a combined annealing/extension step during which the probe hybridizes to the target and the dsDNA-specific 5' to 3' exonuclease activity of Taq or Tth cleaves the oligonucleotide, separating fluorophore from quencher, resulting in a fluorescence signal that is proportional to the amount of amplified product in the sample. A properly designed Hydrolysis probe can be used in combination with additional probes of similar design to determine sequence variations within the amplified target, i.e. genotype.

Molecular Beacons

Molecular beacons are dye-labeled oligonucleotides (25-40 nt) that form a hairpin structure. The 5' and 3' ends have complementary sequences of 5-6 nucleotides that form the stem, while the loop is designed to specifically hybridize to a 15-30 nucleotide section of the target sequence. A fluorescent reporter molecule is attached to one end of the molecular beacon, and a quencher is attached to the other end. When the probe is unbound, hairpin formation occurs, bringing the reporter and quencher into proximity and fluorescence is quenched.

If a target sequence is present during the annealing step of an amplification reaction, the loop portion of the molecular beacon binds to its target sequence, causing the stem to denature. The reporter and quencher are thus separated, quenching is diminished, and the reporter fluorescence is detectable. Because fluorescence is emitted from the probe only when it is bound to the target, the amount of fluorescence detected is proportional to the amount of target in the reaction. Again, a properly designed molecular beacon can be used to distinguish underlying sequence variations, i.e. genotypes, within the amplified sequence. Typically, this is accomplished with melting curve analysis following PCR.

Dual Hybridization Probes

These assays use two sequence-specific oligonucleotide probes which bind to adjacent sequences in the target. The probes are labeled with a pair of dyes that can engage in fluorescence resonance energy transfer (FRET). The donor dye is attached to the 3' end of the first probe, while the acceptor dye is attached to the 5' end of the second probe. This order may be reversed, so long as binding of both oligonucleotides to the target brings the fluorphores within FRET range (Forster radius).

During real-time PCR, excitation is performed at a wavelength specific to the donor dye, and the reaction is monitored at the emission wavelength of the acceptor dye. At the annealing step, the probes hybridize to their target sequences in a head-to-tail arrangement. This brings the donor and acceptor dyes into proximity, allowing FRET to occur. The amount of acceptor fluorescence is proportional to the amount of PCR product present. Hybridization probes enable a variety of genetic detection and quantification readouts.

Primer/Probe Combinations

These detectors use a sequence specific oligonucleotide primer and a sequence specific oligonucleotide probe. The primer and the probe are designed to bind to adjacent sequences of the target, usually with the probe complementary to the strand formed by the primer. The probe and the primer are labeled with a pair of dyes that can engage in (FRET). Generally, the donor dye is attached near the 3' end of the primer, while the acceptor dye is attached to the 3' end of the probe, which anneals to the complementary strand synthesized by primer extension.

As with the dual hybridization probes, during DNA amplification, excitation is performed at a wavelength specific to the donor dye, and the reaction is monitored at the emission wavelength of the acceptor dye. At the annealing step, the probe and primer hybridize to their target sequences in a head-to-tail arrangement. This brings the donor and acceptor dyes into proximity, allowing FRET to occur. The increasing amount of acceptor fluorescence is proportional to the amount of PCR product present.

Dynamic Flux Amplification

One disadvantage of the aforementioned conventional probe chemistries is that they are not compatible with Dynamic Flux Amplification ("DFA") technology. This is due in part to the difference in required melting temperatures of the probes used in PCR as compared to DFA. PCR utilizes probes that are generally in the 20-30 base pair range and generally possess a Tm of at least 20 degrees C. less than the Tm of the sequence of interest. In contrast, DFA requires probes that are within 20 degrees C. or less of the Tm of the sequence of interest. Because DFA normally operates outside of annealing temperature ranges used in probe technology for PCR, such probes as currently practiced are generally not compatible with DFA technology.

Thus, there is a need in the art to develop probe chemistries, reagents, and methodologies, which are compatible with DFA. Specifically, there is an unmet need in the art to develop primers and probes that can be utilized in DFA protocols.

In some aspects, the term "extreme chain reaction" or "XCR" will be utilized in the description. The present inventors utilize the term XCR as a synonym for DFA. Thus, the two terms are used interchangeably.

Multiplex Detection

The need for, at a minimum, the ability to detect two distinct amplified targets within a single reaction is a fundamental aspect of modern diagnostic tests. Although some tests can be brought to market with separate reaction vessels containing the necessary test performance controls, it is cost effective in terms of sample throughput, and reagent usage, to incorporate the reaction controls within a single reaction vessel. Effective utilization of DFA ideally would involve a means to detect one or more amplified targets simultaneously.

Hence, it would be useful to expand probe technology for use with both PCR primers as well as the high Tm and frequently longer primers commonly used in DFA.

It would also be useful to have a probe technology to simultaneously detect more than one amplified target in a single reaction vessel that is compatible with DFA.

SUMMARY OF THE DISCLOSURE

In an embodiment, the disclosure provides a nucleic acid system comprising: a downstream oligonucleotide having a sequence that is complementary to a first target sequence of a target oligonucleotide and that has a cleavable sequence; an upstream oligonucleotide having a sequence that is complementary to a second target sequence of the target oligonucleotide, wherein a 3' end of the upstream oligonucleotide includes an initial nucleic acid polymerase binding site, wherein the downstream oligonucleotide and upstream oligonucleotide anneal to the target oligonucleotide, wherein the downstream oligonucleotide is configured for the polymerase to cleave mononucleotides or small oligonucleotides upon reaching a 5' end of the downstream oligonucleotide.

In an embodiment, the downstream oligonucleotide includes a cleavable sequence that is cleaved by polymerization-independent cleavage by the polymerase that binds with the initial nucleic acid polymerase binding site.

In an embodiment, the downstream oligonucleotide includes a 5' end having a reporter and having a quencher downstream of the reporter.

In an embodiment, the upstream oligonucleotide is a primer.

In an embodiment, the downstream oligonucleotide is not a primer.

In an embodiment, the downstream oligonucleotide is a probe.

In an embodiment, the system comprises a primer having a sequence that is complementary to a sequence of the target oligonucleotide.

In an embodiment, the upstream oligonucleotide and downstream oligonucleotide are hybridized to the target oligonucleotide.

In an embodiment, a complementary oligonucleotide is complementary to and hybridized with the target oligonucleotide, the complementary oligonucleotide having the reverse primer hybridized therewith.

In an embodiment, the downstream oligonucleotide and upstream oligonucleotide anneal to the target oligonucleotide at a sufficiently close nucleotide distance for the nucleic acid polymerase to contact a 5' end of the downstream oligonucleotide when binding to the initial nucleic acid polymerase binding site of the upstream oligonucleotide.

In an embodiment, the upstream oligonucleotide and downstream oligonucleotide are cooperatively configured for the downstream oligonucleotide to be cleaved by polymerization-independent cleavage by the polymerase that binds with the initial nucleic acid polymerase binding site of the upstream oligonucleotide.

In an embodiment, the downstream oligonucleotide and upstream oligonucleotide anneal to the target oligonucleotide at a sufficiently far nucleotide distance for the nucleic acid polymerase to not contact a 5' end of the downstream oligonucleotide so as to leave the sufficiently far nucleotide distance between the upstream oligonucleotide and downstream oligonucleotide when the nucleic acid polymerase binds to the initial nucleic acid polymerase binding site of the upstream oligonucleotide.

In an embodiment, the 5' end of the downstream oligonucleotide cleaves into mononucleotides or small oligonucleotides by the polymerase until the downstream oligonucleotide is sufficiently small to dissociate from the target oligonucleotide.

In an embodiment, the upstream oligonucleotide and downstream oligonucleotide are cooperatively configured for the downstream oligonucleotide to be cleaved by polymerization-dependent cleavage by the polymerase after polymerization.

In an embodiment, the upstream oligonucleotide is a primer and the downstream oligonucleotide is a probe.

In an embodiment, the downstream oligonucleotide includes at least one label that is cleaved by nuclease activity.

In an embodiment, the downstream oligonucleotide includes an upstream label and a downstream label.

In an embodiment, the upstream label comprises a fluorescent dye or quencher, and a downstream label comprises a fluorescent dye and quencher, such that when the downstream oligonucleotide is in solution, the signal from the fluorescent dye is suppressed by the quencher.

In an embodiment, the upstream label comprises a fluorescent dye or quencher, and a downstream label comprises a fluorescent dye and quencher, such that when binding of the upstream oligonucleotide and downstream oligonucleotide to the target oligonucleotide occurs, the polymerase cleaves either the fluorescent label or the quencher of the downstream oligonucleotide, releasing it into the solution such that the dye is no longer subject to the quencher and can fluoresce.

In an embodiment, the upstream label comprises a fluorescent dye or quencher, and a downstream label comprises the other of a fluorescent dye or quencher so that one oligo has the dye and the other has the quencher, such that when the downstream oligonucleotide is in solution, the signal from the fluorescent dye is suppressed by the quencher.

In an embodiment, one of the upstream oligonucleotide or downstream oligonucleotide include a bathophenanthroline-RU II complex as a label.

In an embodiment, one of the upstream oligonucleotide or downstream oligonucleotide include a bathophenanthroline-RU II complex as a label, and the other of the upstream oligonucleotide or downstream oligonucleotide includes an energy donor molecule.

In an embodiment, one of the upstream oligonucleotide or downstream oligonucleotide include a bathophenanthroline-RU II complex as a label, and the other of the upstream oligonucleotide or downstream oligonucleotide includes a lumazine chromophore group as an energy donor molecule.

In an embodiment, one of the upstream oligonucleotide or downstream oligonucleotide include a bathophenanthroline-RU II complex as a label, and the other of the upstream oligonucleotide or downstream oligonucleotide includes an energy donor molecule, wherein one of the labels is cleaved from the downstream oligonucleotide, a change in luminescence is detected.

In an embodiment, the upstream oligonucleotide (forward primer) and reverse primer are configured to have a Tm close to a Tm of the target oligonucleotide or amplicon.

In an embodiment, the upstream oligonucleotide (forward primer) and reverse primer has at least 50 base pairs, or at least 40 base pairs, or at least 30 base pairs, or at least 20 base pairs, or at least 10 base pairs. In embodiments, the upstream oligonucleotide primer has from 5-10 base pairs, or 10-20 base pairs, or 20-30 base pairs, or 30-40 base pairs, or 40-50 base pairs, or 50-60 base pairs, or 60-100 base pairs, or 100-200 base pairs, or 10 or more base pairs, or 20 or more base pairs, or 30 or more base pairs, or 40 or more base pairs, or 50 or more base pairs.

In an embodiment, the downstream oligonucleotide (probe) has at least 50 base pairs, or at least 40 base pairs, or at least 30 base pairs, or at least 20 base pairs, or at least 10 base pairs. In embodiments, the downstream oligonucleotide probe has from 5-10 base pairs, or 10-20 base pairs, or 20-30 base pairs, or 30-40 base pairs, or 40-50 base pairs, or 50-60 base pairs, or 60-100 base pairs, or 100-200 base pairs, or 10 or more base pairs, or 20 or more base pairs, or 30 or more base pairs, or 40 or more base pairs, or 50 or more base pairs.

In an embodiment, target oligonucleotide is longer than a traditional real time PCR target sequence.

In an embodiment, a method of amplifying a target nucleic acid sequence is taught, the method comprising: providing the nucleic acid system of one of the claims; denaturing DNA having the target sequence; hybridizing the upstream oligonucleotide and downstream nucleotides to the target oligonucleotide; hybridizing a primer to the complement oligonucleotide of the target oligonucleotide; extending the upstream oligonucleotide via polymerization with a polymerase toward the downstream oligonucleotide; cleaving nucleotides or small oligonucleotides of the downstream oligonucleotide; and completing polymerization of complements of the target oligonucleotide and compliment oligonucleotide. In an embodiment, the cleavage is polymerization-independent cleavage. In an embodiment, the cleavage is polymerization-dependent cleavage.

In an embodiment, one determines whether or not the target oligonucleotide or target sequence is present in a sample.

In an embodiment, a multiplexing nucleic acid system is provided, comprising: a triplex-forming oligonucleotide (TFO probe) having: a hybridizing polynucleotide sequence that is designed to hybridize to a target sequence of a target oligonucleotide; and a triplex forming region (TFR) associated with the hybridized polynucleotide sequence.

In an embodiment, the TFR includes a sequence configured for triplex base paring.

In an embodiment, the TFO primer forms a triplex with the target oligonucleotide and a third oligonucleotide.

In an embodiment, the hybridizing polynucleotide sequence is configured as a probe nucleotide having a probe moiety.

In an embodiment, the TFR is at the 5' end of the hybridizing polynucleotide sequence.

In an embodiment, the TFR is proximal of the 5' end of the hybridizing polynucleotide sequence.

In an embodiment, the TFR is at the 3' end of the hybridizing polynucleotide sequence.

In an embodiment, the TFR is proximal of the 3' end of the hybridizing polynucleotide sequence.

In an embodiment, the TFR is at a location between the 5' end and 3' end of the hybridizing polynucleotide sequence.

In an embodiment, the hybridizing polynucleotide sequence is configured as a primer sequence.

In an embodiment, the TRF includes a label moiety selected from the group consisting of a fluorescent moiety, radioactive moiety, color moiety, fluorescent reporter moiety, fluorescent quenching moiety, one of a pair of fluorescent resonance energy transfer moieties (e.g., donor moiety or acceptor moiety), and combinations thereof.

In an embodiment, the hybridizing polynucleotide sequence is 50 bases or greater in length.

In an embodiment, the hybridizing polynucleotide sequence ranges from about 20 to about 100 bases in length, or about 100 to about 200 bases in length, or about 200 to about 500 bases in length, or about 500 or more bases. Furthermore, the hybridizing polynucleotide can comprise any range subsumed within the aforementioned. For example, the hybridizing polynucleotide sequence could range from about 100 to about 150 bases in length, or about 150 to about 300 bases in length, or about 200 to about 250 bases in length, or about 250 to about 500 bases in length, or more.

In an embodiment, the TFO probe is hybridized with a TFR the target sequence of a target oligonucleotide.

In an embodiment, the TFO probe is hybridized with the target oligonucleotide by the hybridizing polynucleotide sequence being hybridized to the target sequence of a target oligonucleotide, wherein the TFR is not hybridized with the target oligonucleotide.

In an embodiment, the TFO probe is hybridized with an extended first primer by the hybridizing polynucleotide sequence being hybridized to the target sequence of the extended first primer, an extended polymerized region of the TFO probe being hybridized with the first primer, and wherein the TFR is hybridized to a TRF complementary portion of the extended first primer.

In an embodiment, a 3' phosphate cap is utilized. However, other embodiments utilize any blocker known in the art, for example C-3, C6, C18, etc.

In an embodiment, a label linked to the hybridizing polynucleotide sequence is utilized.

In an embodiment, a cap that inhibits extension from the 3' end is used.

In an embodiment, a 3' or 5' label or donor dye is used.

In an embodiment, the TFO probe is a triplex forming fluorescent probe (TFFP).

In an embodiment, a double stranded nucleic acid having a second TFR, wherein the TFR of the TFO probe forms a triplex with the second TFR such that the TFO probe forms a triplex with the double stranded nucleic acid.

In an embodiment, a double stranded nucleic acid having a second TFR and having a receptor dye, wherein the TFR of the TFO probe forms a triplex with the second TFR such that the TFO probe forms a triplex with the double stranded nucleic acid, and where the TFO probe has a donor dye.

In an embodiment, a double stranded nucleic acid having a second TFR and having a receptor dye, wherein the TFR of the TFO probe forms a triplex with the second TFR such that the TFO probe forms a triplex with the double stranded nucleic acid, and where the TFO probe has a donor dye adjacent a 3' cap.

In an embodiment, a double stranded nucleic acid having a second TFR and having a first label, wherein the TFR of the TFO probe forms a triplex with the second TFR such that the TFO probe forms a triplex with the double stranded nucleic acid, and where the TFO probe has a second label, wherein the first label and second label provide a detectable emission upon close association.

In an embodiment, the TFFP anneals to amplified DNA only when the temperature of reaction is at or below annealing temperature of primers, and thereby the TFFP does not participate in polymerization reaction. However, in some embodiments, the TFFP can be bound to the template anytime the polymerase has extended past the TFR.

In an embodiment, the TFFP bonds to amplified double stranded DNA, and a light is shone thereon, the donor dye on the TFFP resonates, as the donor dye resonates, it transfers energy to an acceptor dye located on the double stranded DNA, causing the acceptor dye to fluoresce at a particular wavelength, emitting light of a color that corresponds to that wavelength so as to indicates that the target sequence was present and has been amplified.

In an embodiment, the TFFP bonds to amplified double stranded DNA, and a light is shone thereon, the donor dye on the amplified double stranded DNA, as the donor dye resonates, it transfers energy to an acceptor dye located on the TFFP, causing the acceptor dye to fluoresce at a particular wavelength, emitting light of a color that corresponds to that wavelength so as to indicates that the target sequence was present and has been amplified.

In an embodiment, a plurality of TFR primers with different target sequences, the TFR primers have different labels.

In an embodiment, a plurality of TFR primers with different target sequences, the TFR primers have different first labels, and a TFO probe includes a corresponding label that causes fluorescence when associated with the different first labels.

In an embodiment, a TFO probe is designed to anneal at approximately the same or lower temperature than a Tm of the TFR primers. However, in other embodiments, the TFO probe can anneal at temperatures normally encountered during routine PCR.

In an embodiment, the target sequence includes a naturally occurring TFR sequence.

In an embodiment, the TFR includes a naturally occurring TFR sequence, and wherein a TFO probe is configured to hybridize with the target sequence and a TFR of the target oligonucleotide.

Embodiments are disclosed that comprise one or more non-specific DNA binding dyes that bind with hybridized triplex DNA.

Embodiments are disclosed that comprise one or more quadruplex binding dyes.

Embodiments are disclosed that comprise a TFO probe that includes a fluorescent dye and quencher.

In some embodiments, a TFO probe includes a fluorescent dye and quencher in a hairpin configuration.

In some embodiments, the TFR creates strands of triplex forming DNA when target DNA includes a sequence having complementarity with the sequence of the TFR.

In some embodiments, the TFR creates strands of triplex forming DNA along the length when target DNA includes a sequence having complementarity with the sequence of the TFR.

In some embodiments, the TFO creates strands of triplex forming DNA appended to a target DNA when the target DNA includes a sequence having complementarity with the sequence of the TFR.

In some embodiments, the target DNA includes a triplex forming region.

In some embodiments, the TFR is added to the multiplexing nucleic acid artificially to the amplified product of an amplification protocol with the multiplexing nucleic acid.

In some embodiments, the TFR is a naturally occurring triplex forming region in the hybridizing polynucleotide sequence.

Also provided herein is a method of amplifying a target nucleic acid sequence, the method comprising: providing the nucleic acid system of one of the claims that includes a TFR primer; hybridizing a TFR primer to the target oligonucleotide, wherein the TFR primer includes a tag having one or more TFRs incorporated into the oligonucleotide; extending the TFR primer by polymerization with a polymerase; de-hybridizing the extended TFR primer from the target oligonucleotide; hybridizing a primer to the extended TFR primer; extending the primer so as to form a complement of the extended TFR primer. Further provided herein is a method of detecting an amplified target sequence, by: providing a nucleic acid system as set forth above that includes a TFO probe; and determining whether the TFO probe bonds with a TFR region in amplified nucleic acids. In some aspects, the TFO probe includes a label to facilitate detection of amplified target sequence. In some aspect, the detection occurs after amplification.

Also provided herein are kits comprising any of the aforementioned oligonucleotides, primers, probes, and reaction agents. A kit having two or more oligonucleotide of one of the claims.

These and other features, aspects, and advantages of embodiments of the present disclosure, will become better understood with regard to the following description, claims, and accompanying drawings, explained below.

BRIEF DESCRIPTION OF THE DRAWINGS

FIG. 20 depicts that in this embodiment the TFO probe utilizes a hairpin dye and quencher configuration.

DETAILED DESCRIPTION

Figure 1:
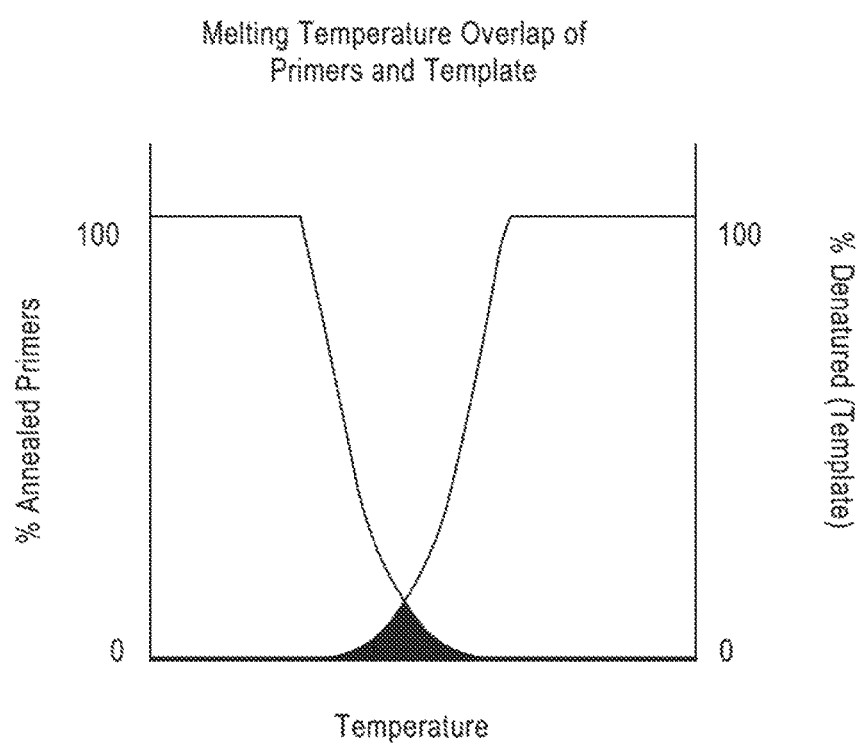
FIG. 1 is a graphical representation of a design for overlapping primer annealing temperatures and template denaturation temperatures.

In the description and tables which follow, a number of terms are used, in order to provide a clear and consistent understanding of the specification and claims, including the scope to be given such terms, the following definitions are provided.

Definitions

The term "a" or "an" refers to one or more of that entity; for example, "a primer" refers to one or more primers or at least one primer. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

The term "microorganism" as used herein can refer to bacteria, archaea, fungi, protozoa, parasites and/or viruses.

The "subject" referred to herein can be any organism capable of hosting a microorganism, including but not limited to, experimental animals (e.g., mice, rats, rabbits, and the like) and humans. In various embodiments, the subject is a human patient suffering from an infectious disease. In other embodiments, the subject is the organism itself, such as the human patient.

A "biological sample" described herein can include any biological material taken from a subject, including, but not limited to, expectorations (e.g., sputum), blood, blood cells (e.g., lymphocytes), tissue, biopsies, cultured cells, pleural, peritoneal, or cerebrospinal fluid, sweat, feces, and urine. In some embodiments, a biological sample from a subject is treated, e.g., to culture an infectious microorganism and/or amplify its genetic material, before being assayed according to methods provided herein.

As used herein, the term "drug" can refer to any compound, agent, treatment modality, or combination thereof. In some preferred aspects, the drug is an antibiotic compound.

The terms "target nucleic acid(s)" as used herein refers to nucleic acids derived from an infectious microorganism, human, mammalians, or plants. In some aspects, a target nucleic acid is a nucleic acid of an organism or a microorganism that is assayed according to a method provided herein.

The term "reference nucleic acid" as used herein refers to a nucleic acid corresponding to a target nucleic acid (e.g., representing the same portion of genomic DNA), that differs from the target nucleic acid by one or more sequence variations. For example, in some aspects, a reference nucleic acid has the sequence of a wild-type microorganism (e.g., with respect to responsiveness to a drug of interest). In further aspects, a reference nucleic acid has the sequence of a wild-type human cell, such as a diseased cell, including, e.g., a human cancer cell.

The term "sequence variation" as used herein in relation to nucleic acids refers to a difference in the sequence of a nucleic acid relative to the sequence of a corresponding nucleic acid (e.g., a sequence representing the same gene or other portion of genomic DNA). In some embodiments, sequence variations detected according to various methods provided herein are "Single Nucleotide Polymorphisms" ("SNPS"), resulting from a difference in the identity of a single nucleotide between a target nucleic acid and a reference nucleic acid. In further embodiments, sequence variations detected according to various methods provided herein include "multiple nucleotide Polymorphisms." In some embodiments, the reference nucleic acid corresponds to a non-drug resistant phenotype and a drug resistant phenotype is detected according to a method provided herein by identifying a sequence variations between the reference nucleic acid and a target nucleic acid of a biological sample from a subject infected with the microorganisms or diseased cell, such as a drug resistance cancer cell.

The terms "responsiveness" and "drug responsiveness" as used herein can refer to resistance, sensitivity, susceptibility, tolerance and/or other phenotypic characteristics of a microorganism or diseased cell, such as a cancer sell, related to the therapeutic effect of a drug, including non-responsiveness. Drug responsiveness can be assessed directly, according to the effect of the drug on a targeted microorganism or diseased cell, such as a cancer cell (e.g., a bacterial mortality or a cellular mortality), and/or indirectly, according to the effect of the drug on one or more aspects of an infectious disease caused by the microorganism (e.g., prevention, amelioration, alleviation, and/or elimination of the disease or one or more symptoms of the disease). In some preferred aspects, systems and methods are provided herein for detecting resistance to one or more drugs, where resistance refers to inheritable (genetic) resistance.

The term "variable sequence element" refers to a region of a nucleic acid (e.g., DNA or RNA) comprised of a string of adjacent nucleotides that includes at least one sequence variation known to be associated with a phenotypic characteristic of interest, such as resistance, sensitivity, and/or other aspects of drug responsiveness or propensity for a particular disease such as cancer or heart disease, or more mundane phenotypic characteristics such as eye color or hair color. For example, a sequence variation associated with drug resistance will often occur in a region of a nucleic acid that encodes a site of the corresponding protein that is a structural and/or functional determinant of drug responsiveness, such as a drug binding site. A variable sequence element including the known variation (and surrounding nucleotides) will likely encode structurally and/or functionally related portions of the protein (e.g., a pocket, fold, or other structure that comprises the drug blinding site), and additional, uncharacterized variations within the variable sequence element will likely be associated with the same phenotype as the known variations.

The terms "nucleic acid" and "oligonucleotide" refer to primers, probes, and oligomer fragments to be detected, and shall be generic to polydeoxyribonucleotides (containing 2-deoxy-D-ribose), to polynucleotides (containing D-ribose), and to any other type of polynucleotide which contains an N glycoside of a purine or pyrimidine base, or modified purine or pyridine base. There is no intended distinction in length between the terms "nucleic acid" and "oligonucleotide", and these terms will be used interchangeably These terms refer only to the primary structure of the molecule. Thus, these terms include double and single stranded DNA, was well as double and single stranded RNA.

The oligonucleotide is not necessarily physically derived from any existing or natural sequence but may be generated in any manner, including chemical synthesis, DNA replication, reverse transcription, or a combination thereof. The terms "oligonucleotide" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalysed. Such conditions include the presence of five different deoxyribonucleoside triphosphates and polymerization-inducing agents such as DNA polymerase or reverse transcriptase, in a suitable temperature. The primer is preferably single stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present disclosure and include, for example, inosine and 7-deasaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

As used herein, the term "allele" is any of one or more alternative forms of a gene which relate to one trait or characteristic. In a diploid cell or organism, the two alleles of a given gene occupy corresponding loci on a pair of homologous chromosomes.

As used herein, the term "amino acid sequence" includes an oligopeptide, peptide, polypeptide, or protein and fragments thereof that are isolated from, native to, or naturally occurring in a plant, or are synthetically made but comprise the nucleic acid sequence of the endogenous counterpart.

As used herein, the term "efficiency" refers to a hallmark of Real-Time PCR assays. An ideal qPCR (quantitative PCR) reaction has an efficiency of 100% with a slope of −3.32, which correlates with a perfect doubling of PCR product during each cycle. However, slopes between −3.1 and −3.6 with efficiencies between 90 and 110% are generally considered acceptable (Commission, C. A. (2009). Definition of Minimum Performance Requirements for Analytical Methods of GMO Testing European Network of GMO Laboratories (ENGL), (October 2008), 1-8). Efficiency is established by replicated standard curves. Amplification efficiency is determined from the slope of the log-linear portion of the standard curve and is calculated as E=(10(−1/slope)−1)*100. (Bustin, S. A., et al. (2009). The MIQE Guidelines: Minimum Informartion for Publication of Quantitative Real-Time PCR Experiments. Clinical Chemistry, 55(4), 1-12. doi:10.1373/clinchem.2008.112797).

As used herein, the term "linearity" refers to a hallmark of optimized Real-Time PCR assays and is determined by the R2 value obtained by linear regression analysis, which should be ≥0.98 (Bustin et al., 2009).

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The terms "target region", "target sequence", and "target nucleic acid sequence" refer to a region of a nucleic acid which is to be detected, quantified, or genotyped.

The term "probe" refers to an oligonucleotide, typically labeled, that forms a duplex structure with a sequence of a target nucleic acid due to complementary base pairing. The probe will comprise a "hybridizing region", preferably consisting of 30 or more nucleotides, and in some instances, consisting of 50 or more nucleotides, corresponding to a region of the target sequence. Ideally, the Tm of the probe will be within 30 degrees or less of the Tm of the sequence of interest. "Corresponding" means identical to or complementary to the designated nucleic acid. The probe, preferably, does not contain a sequence complementary to sequence(s) used to prime the PCR. Generally, the 3' terminus of the probe will be "blocked" to prohibit incorporation of the probe into a primer extension product. "Blocking" can be achieved by using non-complementary bases or by adding a chemical moiety such as biotin, a phosphate group, or a fluorophore to the 3' hydroxyl of the base nucleotide, which may, depending on the selected moiety, serve a dual purpose by also acting as a label for subsequent detection or capture of the nucleic acid attached to the label. Blocking can also be achieved by removing the 3'-OH or by using a nucleotide that lacks a 3'-OH such as dideoxynucleotide.

The term "label" as used herein refers to any atom or molecule which can be used to provide a detectable (preferably quantifiable) signal, and which can be attached to a nucleic acid or protein. Labels may provide signals detectable by fluorescence, phosphorescence, chemiluminescence, electrochemistry, radioactivity, colorimetry, gravimetry, X-ray diffraction or absorption, magnetism, enzymatic activity, and the like.

As defined herein, "5'→3' nuclease activity" or "5' to 3' nuclease activity" refers to that activity of a template specific nucleic acid polymerase including either a 5' to 3' exonuclease activity traditionally associated with some DNA polymerase, whereby nucleotides are removed from the 5' end of an oligonucleotide in a sequential manner, (i.e., *E. coli* DNA polymerase I has this activity, whereas the Klenow fragment does not), or a 5' to 3' endonuclease activity wherein cleavage occurs more than one phosphodiester bond (nucleotide) from the 5' end, or both.

The term "adjacent" as used herein refers to the positioning of the primer with respect to the probe on its complementary strand of the template nucleic acid in which the nucleotides may directly abut one another. Alternatively, for use in the polymerization-dependent process, as when the present method is used in the PCR and DFA and detection methods as taught herein, the "adjacency" may be anywhere within the sequence to be amplified, anywhere downstream of the primer such that primer extension will position the polymerase so that cleavage of the probe occurs.

A "singleplex reaction" means a reaction where only one product is being tested for in a single reaction vessel.

A "duplex reaction" means a reaction where two products are being tested for in a single reaction vessel.

A "multiplex reaction" means a reaction where more than two products are being tested for in a single reaction vessel.

The terms "sequence-specific oligonucleotide" and "SSO" refer to oligonucleotide probes wherein the hybridizing region is exactly complementary to the sequence to be detected. This is known as "stringent hybridization." The use of stringent hybridization conditions under which the probe will hybridize only to that exactly complementary target sequence allows for detection of the specific target sequence. Stringent hybridization conditions are well known in the art (see, e.g., Sambrook, et al., 1985, molecular cloning—A Laboratory Manual, Cold Springs Harbor, N.Y., incorporated herein by reference). Stringent conditions are sequence dependent and will be different in different circumstances.

The Tm is the temperature (e.g., under defined ionic strength and pH) at which 50% of the oligonucleotides have dissociated. Relaxing the stringency of the hybridizing conditions will allow sequence mismatches to be tolerated; the degree of mismatch tolerated can be controlled by suitable adjustment of the hybridization conditions.

The term "subsequence" refers herein to a nucleotide sequence contained within another sequence.

The term "label", as used herein, refers to any atoms or molecule which can be attached to a nucleic acid, and which can be used to provide a detectable signal or to interact with a second label to modify the detectable signal provided by the second label. Labels may be light-emitting compounds which generate a detectable signal by fluorescence, chemiluminescence, phosphorescence, or bioluminescence. In the alternative, labels may provide signals detectable by radioactivity, electrochemistry, colorimetry, or by the absorption of light, producing fluorescence, or may be used to immobilize a product to an array.

The term "fluorophore" refers to compound which is capable of fluorescing, i.e. absorbing light at one frequency and emitting light at another, generally lower, frequency.

The term "bioluminescence" refers to a form of chemiluminescence in which the light-emitting compound is one that is found in living organisms. Examples of bioluminescent compounds include bacterial luciferase and firefly luciferase.

The term "quenching" refers to a decrease in fluorescence of a first compound caused by a second compound, regardless of the mechanism. Quenching typically requires that the compounds be in close proximity. As used herein, either the compound or the fluorescence of the compound is said to be quenched, and it is understood that both usages refer to the same phenomenon.

The term "intercalator" refers to an agent or moiety capable of non-covalent insertion between stacked base pairs in a nucleic acid double helix.

The term "homogeneous", as used herein applied to multi-step processes, refers to methods for carrying out the steps of the process, wherein the need for sample handling and manipulation between steps is minimized or eliminated. For example, a "homogeneous" amplification/detection assay refers to a coupled amplification and detection assay wherein the need for sample handling and manipulation between the amplification and detection is minimized or eliminated.

The term "reaction mixture" refers to a solution containing reagents necessary to carry out the reaction. An "amplification reaction mixture", which refers to a solution containing reagents necessary to carry out an amplification reaction, typically contains oligonucleotides primers and a DNA polymerase in a suitable buffer. Reaction mixtures for specific reactions are well-known in the literature.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into sub-ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Dynamic Flux Amplification

Generally, the present disclosure elates to nucleic acids as well as the devices, systems, and methods for using the same in conjunction with a method of DNA amplification hereinafter referred to as "Dynamic Flux Amplification" or "DFA."

Generally, DFA refers to specific techniques of DNA and RNA amplification. DFA takes advantage of the fact that DNA amplification can take place within a fairly narrow temperature range. Once the Tm of the sequence of interest is determined, the DNA sample may be heated to that temperature or 1 to 5 degrees C. above that temperature. This defines the upper parameter of the heating and cooling cycle. The Tm of either the primers or the probes, (whichever possesses the lower Tm) defines the lower parameter of the heating and cooling cycle, within 1 to 5 degrees C.

In practicing DFA, it is generally preferred to use primers with a Tm as close as possible to the Tm of the sequence of interest so that the temperature may be cycled within a narrow range. The result of this narrow cycling is a dynamic opening and closing of a duplex between complementary nucleic acids comprising the sequence of interest as opposed to the complete, or nearly complete denaturing of the entire DNA strand.

The present existing primers (e.g., primers that were tested) target nucleic acid product that contains fewer non-specific products. Thus, the amplified target nucleic acids products can be overall more specific and sensitive for quantitative PCR and genotyping target detection applications as described herein.

"Rational design" of oligonucleotide primers can include the selection via calculation, experiment, or computation of primers that have the desired melting temperature (Tm). The rational design can include selection of a specific primer sequences with the appropriate CO to obtain the desired Tm.

Also, the rational design can include modifications to the primers that include internucleotide modifications, base modifications, and nucleotide modifications.

DFA Primer Design Methodology

In some embodiments, methods are provided for selecting primers for DFA that flank a variable sequence element of interest on a target nucleic acid.

In some embodiments, primers are selected to have a Tm with the target nucleic acid (primer:target Tm) that is within a narrow range of the Tm of the target nucleic acid (target: target Tm). The specific, narrow temperature range used for such an amplification of the target nucleic acids is dependent on the melting profile of the target nucleic acid, and thereby the sequence of the target nucleic acid being amplified. As such, the narrow temperature range can be used as a target temperature range in order to identify and/or generate specific primers that have sufficiently high Tm values when hybridized with the target nucleic acid.

DFA Primer Design—Overlapping Annealing/Denaturing Curves

Figure 2:
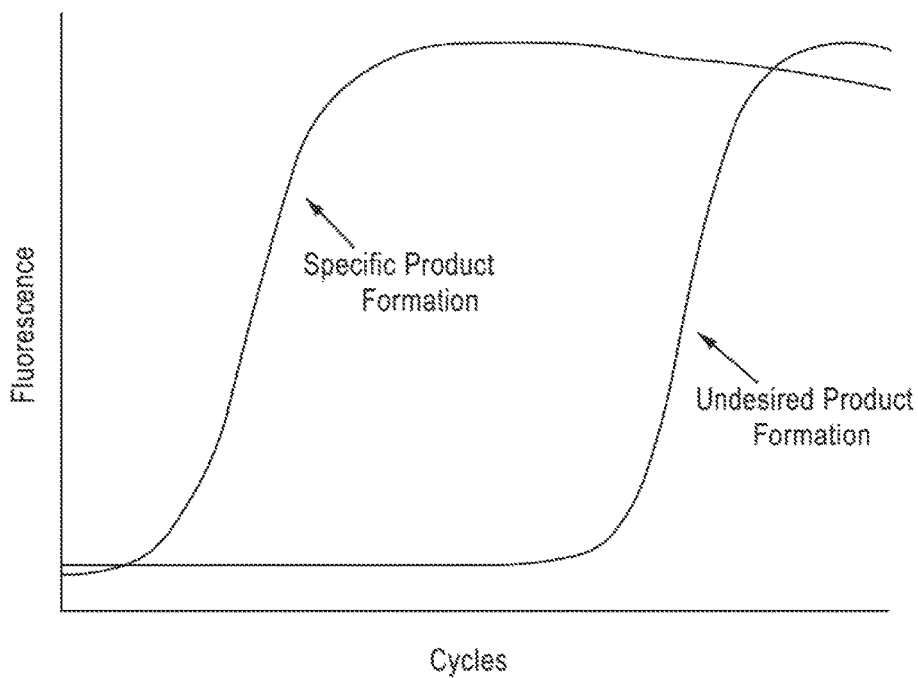
FIG. 2 is an illustration of conventional amplification products by real time PCR.

Accordingly, the Tm values of the primers can be overlapping within the temperature range of annealing and/or denaturing of the target nucleic acid (See, FIG. 1). FIG. 1 can be contrasted with FIG. 2 to illustrate the design of the primers to have the Tm within a range of the Tm of the target nucleic acid. FIG. 2 shows that conventional amplification with primers and a target nucleic acid are devoid of having a temperature overlap (as shown in FIG. 1) and require extreme temperature variations during amplification, corresponding to denaturation, annealing and extension cycles, to produce an amplified product. Such extreme temperature ranges allow for the formation of undesired products.

DFA Primer Design—Iterative Design

In some embodiments, an iterative design process is provided to select and/or optimize primers for specific target nucleic acid sequences to be amplified and/or detected. Advantageously, the iterative method enables the formation of a specific target nucleic acid by using a narrow range of thermal conditions where both the target nucleic acid and the oligonucleotide primers hybridized with the target nucleic acid are in a dynamic flux of annealing and denaturing. Such a dynamic flux of annealing and denaturing can result in a specific amplification of the target nucleic acid with a commensurate decrease in the formation of nonspecific amplification products. The implications of such iterative methods for selecting and/or optimizing primers provides for the use of low cost dyes in lieu of more expensive custom oligonucleotide probes, such as those having fluorescent labels, can allow for quantitative PCR or high resolution denaturation to be used in analyzing the sequence of the target nucleic acid. Also, the iterative method can provide primers that function in the absence of exquisite thermally controlled instruments for the formation of amplification products.

That is, the primers can operate within a narrow temperature range in order to amplify the target nucleic acid, allowing nucleic acid amplification to be used in a much broader range of uses. A number of methods have been described in the art for calculating the theoretical Tm of DNA of known sequence, including, e.g., methods described by Rychlik and Rhoads, Nucleic Acids Res. 17:8543-8551 (1989); Sambrook, J. et al., Molecular Cloning: A Laboratory Manual, Cold Spring Harbor Laboratory Press, Cold Spring Harbor, N.Y. (1989); and Breslauer et al., Proc Natl Acad. Sci. 83: 3746-3750 (1986).

Such an iterative process can include identifying an initial target nucleic acid sequence as the target amplicon, wherein the target nucleic acid sequence can be associated with a particular biological activity, such as possible drug resistance. The target nucleic acid sequence is then amplified in order to produce an amplified product, and the Tm value of the amplified product (e.g., amplicon) is determined using conventional melting curve analysis. The melting curve analysis is then utilized to determine or compute new primers or primer sets for use in the amplification of the target nucleic acid.

The determined or computed primers are then designed with primer Tm values within the range of the melting peak generated by the melt of the amplified product. The primers are then prepared or synthesized to have the designed primer Tm values.

DFA Primer Design—Oligonucleotide Chemical Modification

In some embodiments, primers can be configured to have a Tm that is within a narrow range of the Tm of the target nucleic acid by chemically modifying the oligonucleotides. Well known oligonucleotide synthesis chemistries may be used to increase the Tm values of the primers so they correspond to the temperature range of the Tm of the target nucleic acid. Such chemistries may use modified bases (e.g., Super G, A, T, C), LNA, or PNA, or other such oligonucleotide stabilizing chemistries. Also, additional oligonucleotide hybridization stabilizing chemistries may be developed that can be used for this application.

For example, primers synthesized with both conventional phosphodiester linkage chemistry, and LNA chemistries have been used to provide primer Tm values close to the Tm values of the target nucleic acid sequence. However, it is possible that certain target nucleic acids may have Tm values lower than that of the primers, and a hybridization destabilizing chemistry may need to be included to decrease the primer Tm values so that the primer Tm value is within a range of the Tm values of the target nucleic acid sequence.

DFA Primer Design—Melting Curve Analysis

In some embodiments, methods are provided for refining the design of the primers to minimize the temperature range for the specific amplification of the target nucleic acid sequence. As such the target nucleic acid is amplified with standard reaction thermal cycling conditions to ensure the target nucleic acid sequence is amplified. The amplification is monitored using real-time PCR with a double-stranded DNA binding dye, such as SYBR, LCGreen, LCGreen+, Eva dye, or the like.

The amplified target nucleic acid is subjected to a melting curve analysis to determine the actual Tm value of the target nucleic acid sequence. The melting peak, which can be expressed as $-dF/dT$, is generated from melting the amplified target nucleic acid and can have a range similar to a distribution curve across a defined temperature range. At the low temperature end, the amplified target nucleic acid template is partially denatured. At the uppermost temperature the entire sample of amplified target nucleic acid is denatured. The temperature necessary to denature the target nucleic acid during the amplification procedure is within this temperature distribution.

Initially, the uppermost temperature is recommended to ensure more complete denaturation. Subsequently, the lowermost temperature of the distribution curve can be used as the initial Tm for a set of designed primers for use in amplification before any iterative changes are made to the primers.

Confirmation of the narrow temperature range that the initial primers may be used with can be performed either in serial or in parallel experiments of ever increasing annealing temperatures.

Alternatively, the individual primers can be added to the amplified template and an additional melting curve analysis can be performed on the combined primer and template melting curves.

In any event, the Tm of the primers can be configured to overlap with a narrow temperature range that contains the Tm of the target nucleic acid sequence. The highest annealing temperature from these experiments where the target nucleic acid sequence is amplified specifically and efficiently can be considered the temperature which defines the optimal annealing temperature for the existing primers (e.g. pimers that were tested). These same primers or slightly modified primers can then be resynthesized with additional hybridization stabilizing chemistries. Modifications to the primers to change the Tm in the desired direction so that the primer Tm overlaps with a narrow temperature range that contains the Tm of the target nucleic acid sequence. This can be accomplished using online design tools, such as the LNA design tool available from Integrated DNA Technologies. Such design tools can be used to estimate the number of necessary LNA modifications required to raise the Tm of the primer to better overlap with the melting curve of the target nucleic acid sequence.

In the instance the primer Tm values are greater than the highest melting temperature of the target nucleic acid sequence, it may be necessary to redesign the primers to have a lower Tm. Alternatively, the quantity of divalent and/or monovalent cation salts or other destablizing agents (e.g., AgCl, DMSO, etc.) that are used in the amplification protocol (e.g., PCR) may be reduced to destabilize the hybridization of these oligonucleotides to the template. In any event, a reduction in the primer Tm may be needed in some instances.

DFA Primer Design—GC Content Modification

In some embodiments, the primer Tm can be modified by altering the GC content of the primer sequence. By changing the GC content, the primer Tm can be selectively changed. Usually, increasing the GC content can increase the Tm, and decreasing the GC content can decrease the Tm. However, there are instances that a high GC content is desired that will overly increase the Tm. In such instances, destabilizers can be used to enable the inclusion of high GC content primers or for the use of high GC content target nucleic acid sequences. The destabilizers can selectively decrease the temperature of the amplification procedure. Examples of destabilizers include DMSO, AgCl, and others.

DFA Thermal Cycling Ranges

In some embodiments, the primers can be prepared so that the target nucleic acid amplification or enrichment protocols can be performed at minimized temperature differences during the thermal cycling. This allows the thermal cycling to be done within a narrow temperature range so as to promote the formation of a specific product.

One range of thermal cycling can be within about 15° C. of the target nucleic acid Tm, or within 10° C. of the target nucleic acid Tm, or within 5° C. of the target nucleic acid Tm, or within 2.5° C. of the target nucleic acid Tm, or within 1° C. of the target nucleic acid Tm or even substantially the same Tm as that of the target nucleic acid Tm.

In some embodiments, the thermal cycling conditions for the amplification of the target nucleic acid spans the range of the Tm peak+/−about 1° C. to 15° C. of the target nucleic acid sequence In some embodiments, the thermal cycling conditions for the amplification of the target nucleic acid spans the range of the Tm peak+/−about 1° C. to 10° C. of the target nucleic acid sequence.

Or, in some embodiments, the thermal cycling conditions for the amplification of the target nucleic acid spans the range of the Tm peak+/−about 1° C. to 5° C. of the target nucleic acid sequence.

In some embodiments, the thermal cycling conditions for the amplification of the target nucleic acid spans the range of the Tm peak+/−about 5° C. to 15° C. of the target nucleic acid sequence.

In some embodiments, the thermal cycling conditions for the amplification of the target nucleic acid spans the range of the Tm peak+/−about 5° C. to 10° C. of the target nucleic acid sequence.

In some embodiments, the thermal cycling conditions for the amplification of the target nucleic acid spans the range of the Tm peak+/−about 5° C. of the target nucleic acid sequence.

In some embodiments, the thermal cycling conditions for the amplification of the target nucleic acid spans the range of the Tm peak+/−about 2.5° C. of the target nucleic acid sequence.

Such narrow temperature ranges make it possible to amplify specific target nucleic acids without thermal cycling between temperatures corresponding to the normal stages of PCR amplification (denaturation, annealing, and extension).

Also, it makes it possible to perform amplifications and enrichments in commercial temperature-controlled instruments that can be set at selected temperatures or be varied within narrow temperature ranges, such as an oven, heating block, or the like.

Figure 3:
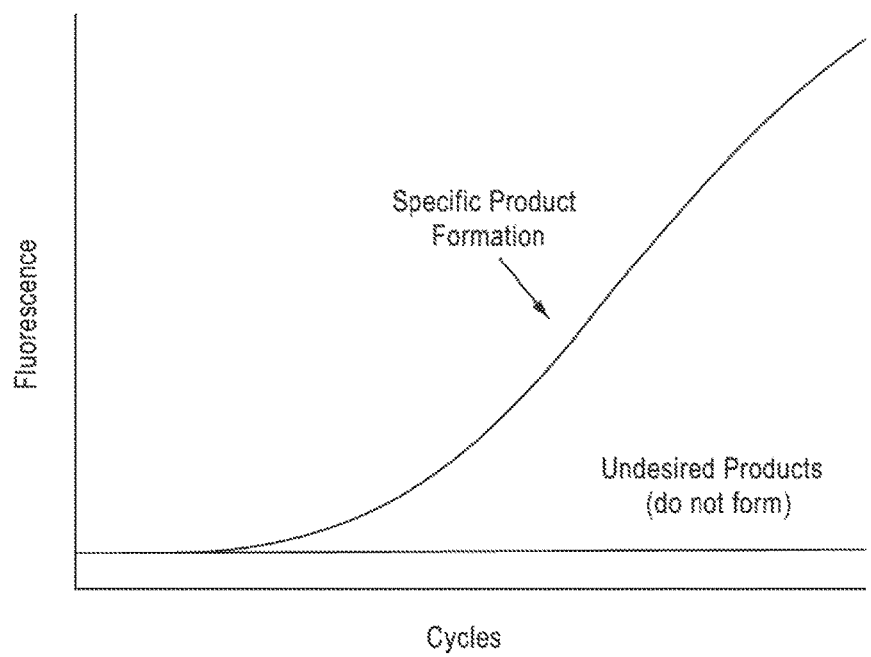
FIG. 3 is a graph showing high temperature PCR amplification of the same template used in FIG. 2.

FIG. 3 illustrates the graph of a narrow temperature range PCR amplification with the same target nucleic acid sequence as shown in FIG. 2, which shows more specific product formation and less undesired products are formed.

In some embodiments, the temperatures of the thermocycling can be selected in a narrow temperature range to substantially limit amplification to amplifying the target nucleic acid sequence. As such, the thermal cycling conditions can be modified to amplify the target nucleic acid sequence by modifying the annealing temperature to be substantially the same as the lower temperature base of the melting peak for the amplicon. Also, the thermal cycling conditions can be modified to amplify the target nucleic acid sequence by modifying the annealing temperature to be substantially the same as the higher temperature base for the melting peak of the amplicon.

In some embodiments, the primer Tm can be selected so that the amplification of the target nucleic acid can be performed at a temperature that ranges between about 75° C. to about 90° C. Such a temperature range, or narrowed 5° C. to 10° C. range therein, can be used for the amplification of DNA and/or RNA target nucleic acid sequences to reduce the formation of non-specific products during the amplification (e.g., PCR) process.

In some embodiments, the primer Tm can be selected so that the amplification is performed at isothermal amplification conditions in the Tm range of the target nucleic acid sequence to ensure appropriate product formation.

In some embodiments, the present disclosure includes a method of designing a primer set having a Tm with a target nucleic acid that is within a narrow range from the Tm of the target nucleic acid sequence. As such, the primer set can be designed so that the primer Tm overlaps the distribution curve of the Tm of the target nucleic acid sequence. For example, the primer set can be used in real-time PCR assays so that the primer Tm overlaps the distribution curve of the Tm for the target nucleic acid sequence so that a narrow temperature range can be used to amplify the target nucleic acid sequence.

DFA pH Modification

In some embodiments, the conditions of the protocol for amplifying the target nucleic acid sequence can be modified to an appropriate pH to increase the specificity of selectively amplifying the target nucleic acid over other nucleic acids. As such, the use of an appropriate pH can increase the ability to selectively amplify the target nucleic acid sequence. This can include the use of an amplification buffer that can enable the activation of chemically inactivated thermal stable DNA polymerases. Also, adjusting the pH with selected amplification buffers can allow for the amplification protocol to be performed at reduced temperatures, such as those temperatures ranges that have been recited herein.

In some embodiments, the pH of the amplification buffer can be adjusted so as to allow for the conversion of a chemically inactivated enzyme to the activated state. As such, an enzyme may be activated in a slightly acidic condition; however, basic pH values may be used for some enzymes. For acid-activated enzymes, standard Tris-based PCR buffers can have significant temperature dependence (e.g., reducing by 0.028 pH units per degree C.). Complete activation of the enzyme (e.g., chemically inactivated thermal stable DNA polymerase) from the inactivated state can require the pH to be less than about 7, more preferably less than about 6.75, and most preferably less than 6.5.

In some embodiments, the amplification protocol includes the use of lower pH buffers so that the amplification can be performed at lower activation temperatures. For example, for every 10° C. below 95° C., the enzyme activation temperature can be lowered by 0.3 pH units. However, limits to this approach are entirely a function of the dye chemistry used for the real-time detection of the amplified template (e.g., Fluorescein-based detection has significantly reduced fluorescence below pH 7.3).

DFA Modulation of Amplicon Size

In some embodiments, the design of the primers and/or amplification conditions can be modulated so as to modulate the size of the target nucleic acid sequence being amplified. This can include modulating the design of the primers and/or amplification conditions so that the size of the amplicon is significantly larger than that of the combined primers only. This can include the amplicon being 1-3 nucleotides longer than the primers, or 2 times larger than the primers, or 5 times larger than the primers, and more preferably 10 times larger than the primers.

DFA Arrays

In some embodiments, the primers designed as described herein can be employed in an array of amplification procedures with different concentrations of starting material. That is, the starting material can be partitioned into an array at varying concentrations, and the primers can be used therewith for the narrow temperature amplification protocol as described herein.

The use of the primers and narrow temperature amplification protocol with an array of varying concentrations of starting material can be used for quantification of the amount of target nucleic acid in the starting material.

Figure 4:
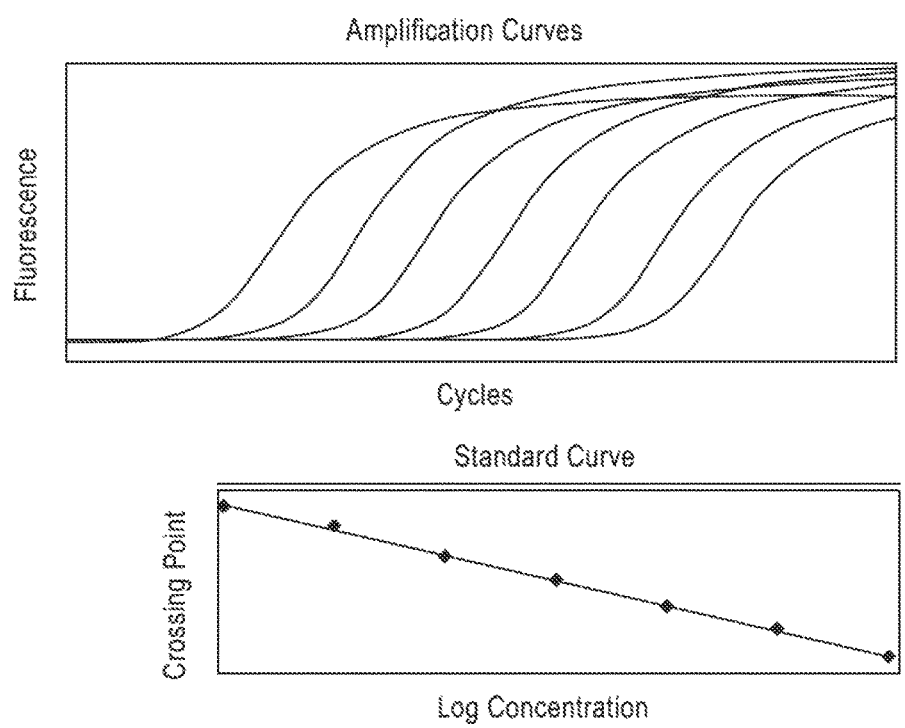
FIG. 4 is a graph showing the HTPCR amplification of the same template material using different starting material concentrations.
Figure 5:
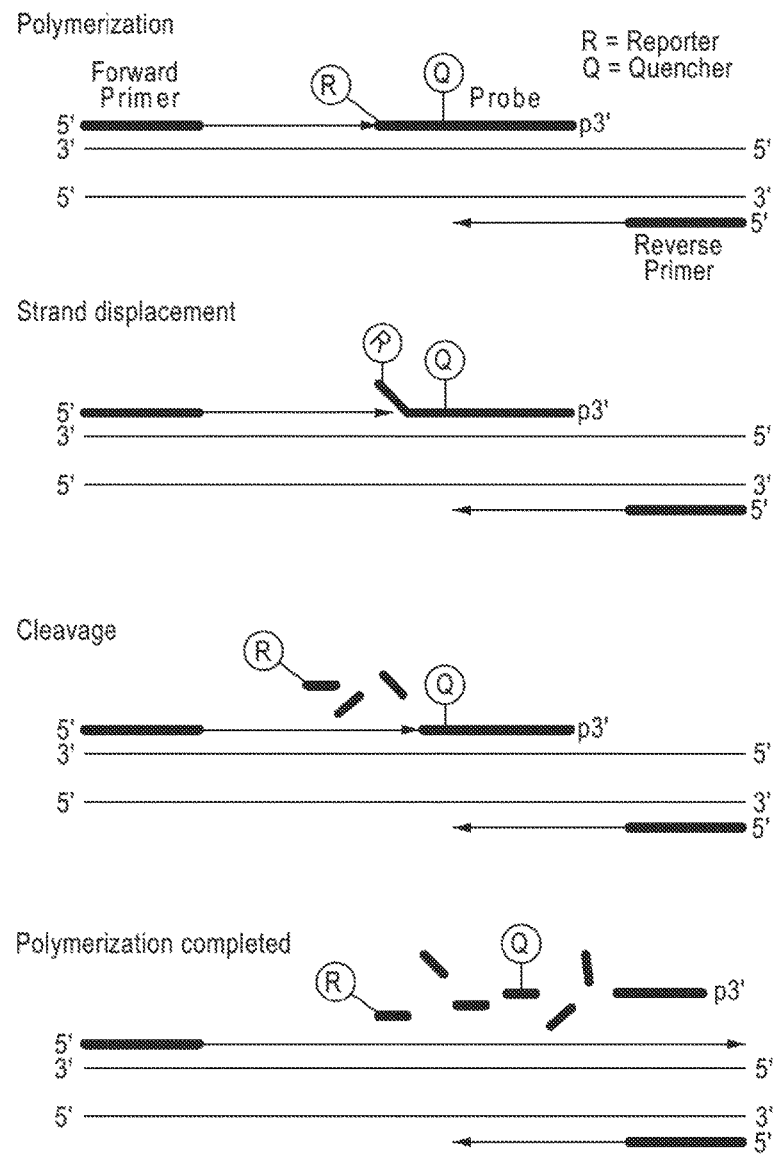
FIG. 5 is a general embodiment of cleaved probe technology according to the disclosure.

FIG. 4 is a graph that shows the use of the primers and protocol with an array of varying concentrations of starting material so that the amount of target material can be quantified.

Target Nucleic Acid Amplification Enrichment

In some embodiments, methods provided herein include a step of amplifying or enriching the target nucleic acid. Such a method can include a procedure substantially similar to well known methods of whole genome amplification and whole transcriptome amplification.

This can include amplifying a genome with a genome library generation step, which can be followed by a library amplification step. Also, the library generating step can utilize the specific primers or mixtures of the specific primers described herein with a DNA polymerase or Reverse Transcriptase. The specific primer mixtures can be designed with the primers so as to eliminate ability to self-hybridize and/or hybridize to other primers within a mixture, but allow the primers to efficiently and frequently prime the target nucleic acid sequence, wherein the primers can be designed as described herein.

In some embodiments, methods are provided for simultaneously determining a genetic expression profile for an individual member of a species relative to an entire standard genome for the species. The methods can comprise distributing a liquid sample of genomic material into an array of reaction chambers of a substrate. The array can comprise a primer set and a probe for each target nucleic acid sequence along the entire standard genome. The liquid sample can comprise substantially all genetic material of the member. Each of the reaction chambers can comprise the primer set and the probe for at least one of the target nucleic acid sequences and a polymerase. The methods can further comprise amplifying the liquid sample in the array, detecting a signal emitted by at least one of the probes, and identifying the genetic expression profile in response to the signal.

Since the isolation of suitable quantities of microorganisms, such as MTb, from sputum samples can be a significant challenge, the genome amplification techniques described herein can be used instead of traditional culturing and purification protocols. Although many molecular diagnostic techniques enable the detection of very small quantities of starting genetic material (e.g., as low as a single copy of a target nucleic acid sequence), it is often difficult to ensure that a particular sample actually contains the desired single copy of the target nucleic acid sequence.

To enable very rare or precious samples to be tested accurately in molecular diagnostic procedures, a technique known as whole genome amplification has been employed to enrich the starting material for use in the downstream molecular diagnostic procedures. The method described here applies the whole genome amplification method to the problem of MTb screening of sputum samples which often contain such low quantities of live organism. Otherwise, standard procedures may use isolates ofMTb that must be grown for up to 2 months to ensure sufficient quantities of genetic material can be obtained from the sample for molecular diagnostic applications.

Using whole genome amplification techniques developed for the in vitro enrichment of rare and precious DNA and/or RNA samples, a novel genetic material enrichment method has been developed to enrich samples containing a microorganism DNA, such as MTb DNA. This technique enables the circumvention of conventional culturing methods that have heretofore been used to increase concentrations of microorganisms, which are often required for downstream molecular diagnostics. Such a whole genome amplification technique uses small quantities of genomic DNA from directly lysed microorganism samples. Samples containing live microorganism that have been isolated using the Petroff method can be directly lysed by a commercially available product, and the resulting small quantities of microorganism DNA can be subjected to the whole genome amplification techniques to provide an amplicon for use in downstream molecular diagnostic applications.

While the procedure for employing the whole genome amplification technique is described with respect to MTb, it is recognized that such a technique can be applied to any microorganism. Using a conventional live organism preparation method, the Petroff method, the isolated MTb is fractionated from the sputum sample leaving small quantities of the organism in a suspension of water. Following the protocol of the manufacturer of the mycobacterium lysis solution, MycoBuffer, (RAOGene; Milford, Pa.), small quantities of MTb DNA are isolated in the residual material from the MycoBuffer product.

Using this directly lysed DNA sample and combining it with reaction ingredients similar to those used in whole genome amplification procedures enables the dynamic opening and closing of a nucleotide that has been referred to as "breathing" or "flux," of complementary nucleic acids. This flux enables access by and binding by, specific primers and probes only, as only those regions in flux can be interrogated by the primers or probes. This, in turn, makes it so the amplification is wholly specific and subsequently the formation of non-specific products (NSP) is substantially eliminated.

The DFA technique has been validated against a variety of DNA templates, and it has been determined that DFA works over a broad range of G+C content templates from 30-66%, where the DFA technique performed comparably in sensitivity to PCR and without the formation of non-specific products (NSPs). DFA has been adapted to the following detection techniques: real-time PCR (dsDNA binding dye), gel-electrophoretic, chemiluminescent, colorimetric, and ELISA.

DFA Probes and Primers

A distinct feature of DFA probes and primers is possession of melting temperatures (Tm) that are close to the Tm of the target sequence. To satisfy this operating parameter, the primers and probes generally must possess higher Tm than those used in PCR amplification. As a consequence, common probe designs used for PCR generally cannot work with DFA, particularly if a real time readout is desired. Hence, the following specification describes primer and probe designs, as well as probe and primer combinations that can be used with DFA.

In one or more embodiments, the technology described involves modifications of existing probe and primer technology to function with DFA.

In other embodiments, the technology described minimizes the number of probes and primers required for DFA operation. The oligonucleotides can be configured and used to limit the number of different oligonucleotides present during the reactions.

Many specific probe designs and probe label combinations are discussed in the literature and known to those of average skill in the art. These include, but are not limited to, the technologies set forth in the following patents: U.S. Pat. Nos. 5,491,063; 5,538,848; 5,571,673; 5,573,906, and 5,804,375, which are each incorporated by specific reference in their entirety.

i. DFA Cleaved Probe Technology—Considerations

For exemplary reasons, one embodiment of the disclosure is based on cleaved probe technology, illustrated generally in FIG. 5 and set forth as follows. Cleaved probe technology refers to any of several strategies that may be employed to distinguish the uncleaved labeled oligonucleotide from the cleaved fragments thereof. In this manner, cleaved probe technology permits identification of those nucleic acid samples which contain sequences complementary to the upstream and downstream oligonucleotides.

The present DFA cleaved probe technology embodiment is a modification of existing cleaved probe technology. For background purposes, cleaved probe technology is described as follows. Cleaved probe technology is based on a 5' to 3' nuclease activity whereby the nucleic acid polymerase can cleave a mononucleotide or small oligonucleotides from an oligonucleotide (e.g., downstream oligonucleotide) annealed to its target oligonucleotide. In order for cleavage to occur efficiently, an upstream oligonucleotide must also be annealed to the same target oligonucleotide.

The 3' end of this upstream oligonucleotide provides the initial binding site for the nucleic acid polymerase. As soon as the bound polymerase encounters the 5' end of the downstream oligonucleotide, the polymerase can cleave mononucleotides or small oligonucleotides therefrom.

The two oligonucleotides can be designed such that they anneal in close proximity on the complementary target nucleic acid such that binding of the nucleic acid polymerase to the 3' end of the upstream oligonucleotide automatically puts it in contact with the 5' end of the downstream oligonucleotide in a process known as "polymerization-independent cleavage."

Alternatively, if the two oligonucleotides anneal to more distantly spaced regions of the template nucleic acid target, polymerization must occur before the nucleic acid polymerase encounters the 5' end of the downstream oligonucleotide. As the polymerization continues, the polymerase progressively cleaves mononucleotides or small oligonucleotides from the 5' end of the downstream oligonucleotide. This cleaving continues until the remainder of the downstream oligonucleotide has been destabilized to the extent that it dissociates from the template molecule in a process that is called "polymerization-dependent cleavage."

In practice, the upstream oligonucleotide comprises the primer and the downstream oligonucleotide comprises the probe.

The probe contains at least one label which is cleaved by the nuclease activity. In some embodiments, the probe comprises an upstream label and a downstream label. The upstream label comprises a fluorescent dye or quencher, and the downstream label comprises a fluorescent dye or quencher, such that when the probe is in solution, the signal from the fluorescent dye is suppressed by the quencher. Thus, when the upstream label comprises a fluorescent dye, the downstream label comprises a quencher, and vice verse.

When binding of the probe and primer to the target oligonucleotide occurs, the polymerase cleaves either the fluorescent label or the quencher, or both releasing them into the solution such that the dye is no longer subject to the quencher and can fluoresce.

In designing the primer and probe combination to utilize probe technology polymerase in the case of DFA, the following factors must be taken into consideration.

First, because one of the central features of DFA is the close proximity between the Tm of the primers and the Tm of the sequence of interest, the primers must frequently be longer than the primers used in PCR. In embodiments, the primers are frequently 50 base pairs, more or less.

Second, because the probes must also anneal at approximately the same or slightly higher temperatures than the primers, they are frequently longer than the probes used in PCR. In embodiments, the probes must also be 50 base pairs or greater.

Third, in order to accommodate probes and primers of this length, the target sequence must be longer than that of PCR. These lengths may vary somewhat depending on the GC content of the respective probes and primers.

Figure 6:
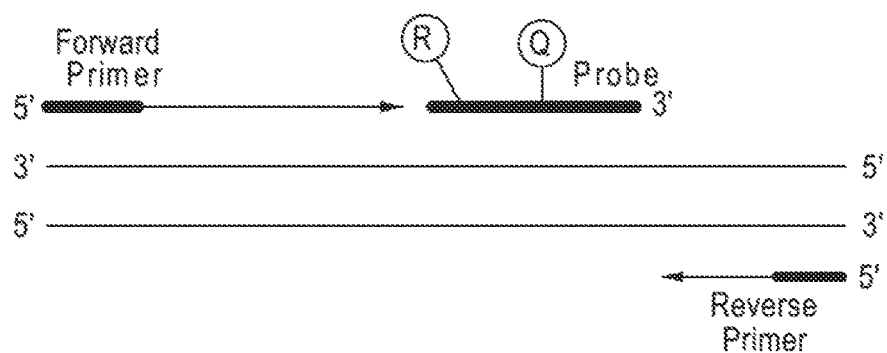
FIG. 6 depicts a general primer and probe combination used in PCR amplification.

FIG. 6 depicts a general primer and probe combination used in PCR amplification. The sequence of interest is generally 100 to 200 base pairs long. The primers generally are 15 to 20 base pairs long and the probes are generally 20 to 25 base pairs long. The probes and primers generally have a melting temperature that is within 30 degrees C. or greater than the melting temperature of the sequence of interest.

The longer probe length creates a problem in using existing cleaved probe chemistry with DFA for the following reason. Quenching generally follows the following formula: $F=1/r^3$.

Thus, in the case of existing cleaved probe chemistries, the quencher is generally sufficiently close radially to the fluorophore that, when the probes are in solution, quenching effectively takes place. In the case of DFA probes, the quencher is generally not sufficiently close radially to the fluorophore to quench when the probes are in solution.

Thus, in the case of traditional cleaved probe chemistries, it is impossible to distinguish between cleaved probes and probes still in solution.

A solution to this problem is herein referred to as "hybrid hairpin/cleaved probes" or simply "hybrid probes."

ii. DFA Cleaved Probe Technology—Hybrid Hairpin/Cleaved Probes

Specifically, these hybrid hairpin/cleaved probes are similar to traditional hairpin probes in that the oligonucleotide strand comprising the probe contains at least one pair of complementary sequences. When the probe is in solution, the complementary sequences intramolecularly hybridize to each other, causing the probe to take on a hairpin like shape and thereby brining the quencher into sufficient radial proximity to the fluorophore to quench the signal from the fluorophore.

The following comprise exemplary sequences for a DFA oligonucleotide probe that will form a hairpin:

Structure 1 Folding bases 1 to 72 of mfoldExample1 (SEQ ID NO: 1)

```
dG = -2.98  dH = -84.20  dS = -261.87  Tm = 48.4 ° C.
            10           20
.-ACCTCCAATGCC|       ACTCC
              AAACATT      T
              TTTGTAA      T
\ ------------^       CTCAG
                           30
40       50
CCTGT   CGATGCGCT
    GCCA         T
    CGGT         A
C----     ACCCAGATT
   70        60
```

Structure 1 Folding bases 1 to 67 of mfoldExample2 (SEQ ID NO: 2)

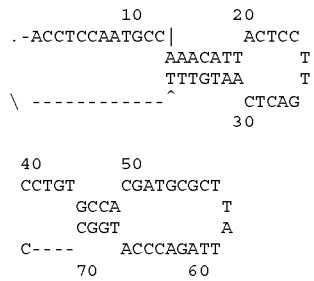

Structure 1 Folding bases 1 to 83 of mfoldExample3 (SEQ ID NO: 3)

```
dG = -3.35  dH = -101.40  dS = -316.14
Tm = 47.6 ° C.
             10              20
.-ATGGACGTGGCTT|         T
                    AGCGTA A
                    TCGTAT T
\ -------------^         T 30           40          50
.-GATGGAAAAATGGTAA       GCT
                    ACGAA    \
                    TGCTT    T
\ ----------------       GAT
                    60

70
CAAGG    GG
    CTT    \
    GAA    C
TCGTT    AT
    80
```

Structure 2 Folding bases 1 to 83 of mfoldExample3 (SEQ ID NO: 4)

```
dG = -2.92  dH = -94.60  dS = -295.60  Tm = 46.9 ° C.
             10          20
.-ATGGACGTGGCTT         T
                   AGCGTA A
                   TCGTAT T
\ -------------         T 30         40         50          60
GATGGAAAAATGGTAAACGAAG|       TCGTCA
                         CTTTAGT    \
                         GAAATCG    A
TCGTT-----------------^       GTTCGG
     80                            70
```

Structure 1 Folding bases 1 to 67 of mfoldExample4 (SEQ ID NO: 5)

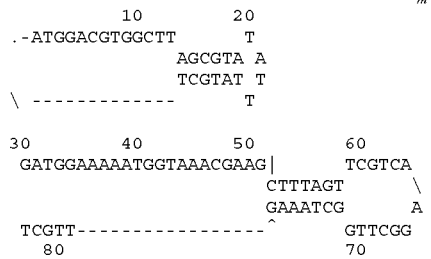

```
         C  GGGGTA    A
T-  G          GGAC
            60
```

Structure 1 Folding bases 1 to 38 of LTSOW_SNP2CT_xm1 (SEQ ID NO: 6)

```
dG = -2.40  dH = -75.20  dS = -234.73  Tm = 47.2 ° C.
            10
TG--|   TCC      TTTC
    GCAA   CAGGT      T
    CGTT   GTCCA      T
AACT^   T--      TCTT
         30         20
```

Structure 7 Folding bases 1 to 36 of LTSOW_TERT_XM1 75-90 (SEQ ID NO: 7)

```
dG = -0.79  dH = -30.80  dS = -96.76  Tm = 45.2 ° C.
10
C---------| A    ATCCCC
           AG  CCC       \
           TC  GGG         C
TCCTCCGGTA^  A     AGTGGA
         30       20
```

Structure 1 Folding bases 1 to 30 of LTSOW_R-NAseP_XM1 (SEQ ID NO: 8)

```
dG = -2.25  dH = -22.40  dS = -64.97  Tm = 71.6 ° C.
            10         20
TCAATGGCTGAGGTGAGGTAC|   G
                     CCC  \
                     GGG   C
--------------------^   A
                    30
```

Structure 1 Folding bases 1 to 42 of LTSOW_CC3_XM1 (SEQ ID NO: 9)

```
dG = 0.02  dH = 40.30  dS = -130.00  Tm = 36.8 ° C.
           10       20
TTTGCT|       AGTTCCCCCTGT
      CTGAG              C
      GACTC              C
------^       CCTTCCACCTCC
      40         30
```

Structure 1 Folding bases 1 to 45 of LTSOW_CYPD2D_XM1 (SEQ ID NO: 10)

```
dG = -3.06  dH = -31.50  dS = -91.70  Tm = 70.4 ° C.
            10        20
TGCAAGAGTCACCAAAATT|   G
                   GCC  A
                   CGG  G
ACCCTACGATTGACCC---^   A
       40        30
``` mfold Version 3.5
M. Zuker, Rensselaer Polytechnic Institute

However, the hybrid probes differ from traditional hairpin probes in the following manner. Unlike traditional hairpin probes, the hybrid comprises sequences on their ends that are complementary to the opposite sequences on the DNA strand to which the probe anneals. This causes the probe to anneal completely to the target sequence, the same or similar manner of a cleaved probe. Thus, like a cleaved probe, the hybrid probe is cleaved as the polymerase extends the sequence. This differs from traditional hairpin probes in that the ends of traditional hairpin probes, are deliberately designed to not complement their opposite target sequence. This is done to allow the polymerase to move under the probe.

The following are examples of hybrid/hairpin probe designs and their complementary DNA sequences.

```
Ex. 1.
                                        (SEQ ID NO: 62)
GCACATAAGTTGATAATTAGTGAGTTGGGTGATACATACACAAGGGT -
Primer
                                        (SEQ ID NO: 63)
CGTGTATTCAACTATTAATCACTCAACCCACTATGTATGTGTTCCCA -
Target
                                        (SEQ ID NO: 64)
GGTTGAAGAAGTTGAGGAAGAGGTTGAAGAAGTGCTGAG - Primer
                                        (SEQ ID NO: 65)
CCAACTTCTTCAACTCCTTCTCCAACTTCTTCACGACTC - Target
                                        (SEQ ID NO: 66)
5'FAM-AGAAATCTCGTGCCCAAACCTGGTGATGGATCC-3'BHQ1-
Probe
                                        (SEQ ID NO: 67)
TCTTTAGAGCACGGGTTTGGACCACTACCTAGG - Target
                                        (SEQ ID NO: 68)
5'Dye-AGAAATCTCGTGCCCAAACCTGGTGATAATCC-3'quencher-
Probe
                                        (SEQ ID NO: 69)
TCTTTAGAGCACGGGTTTGGACCACTACTTAGG - Target
Ex. 2.
                                        (SEQ ID NO: 70)
ATGTAAGGAAGTCCAAATGTTCACCTGAAGACAACTGTGGT - Primer
                                        (SEQ ID NO: 71)
TACATTCCTTCAGGTTTACAAGTGGACTTCTGTTGACACCA - Target
                                        (SEQ ID NO: 72)
GCCTCTGGCAACAGTAAAGCAGGGGCAT - Primer
                                        (SEQ ID NO: 73)
CGGAGACCGTTGTCATTTCGTCCCCGTA - Target
                                        (SEQ ID NO: 74)
5'FAM-TGGCAATCCCAGGTTCTCTTTTCTACCTGTTTGCTCAA-3'
BHQ1-Probe
                                        (SEQ ID NO: 75)
ACCGTTAGGGTCCAAGAGAAAAGATGGACAAACGAGTT - Target
                                        (SEQ ID NO: 76)
5'Dye-TGGCAATCCCAGGTTTTCTTTTCTACCTGTTTGTCAA-3'
quencher-Probe
                                        (SEQ ID NO: 77)
ACCGTTAGGGTCCAAAAGAAAAGATGGACAAACAGTT - Target
```

Figure 7:
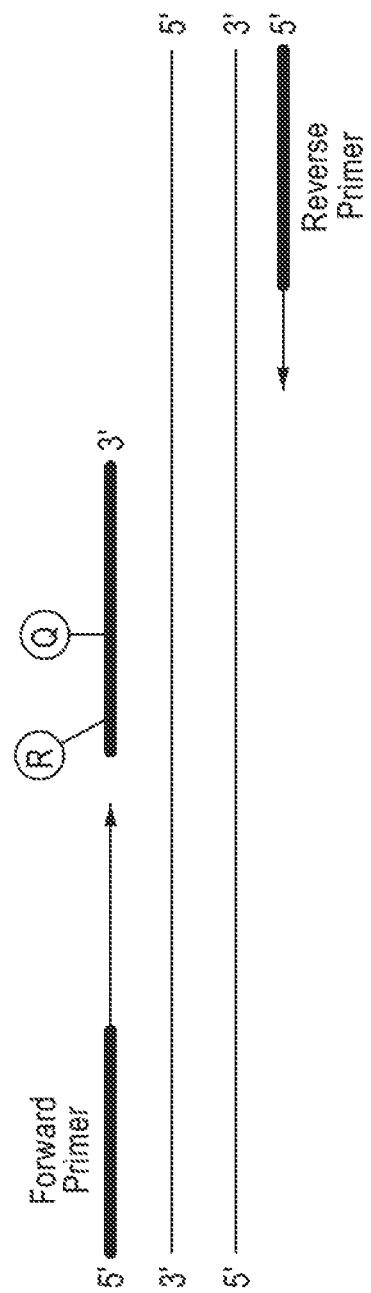
FIG. 7 depicts one embodiment of a primer and probe combination that can be used with DFA.

FIG. 7 depicts one embodiment of a primer and probe combination that can be used with DFA. It depicts one method for obtaining a melting temperature for the probes and the primers that is close to the melting temperatures for the sequence of interest. In this embodiment, the probes and primers are generally 50 base pairs in length or greater. In order to accommodate primers and probes of this length, the sequence of interest is generally 250 to 300 base pairs in length. This gives the difference in melting temperature between the primers, probes, and sequence of interest of 20 degrees C. or less.

In another embodiment, the melting temperature of the primers and probes may be increased without significantly increasing oligonucleotide length by covalently coupling agents which bind to single- or double-stranded DNA, thereby increasing the Tm. A class of agents known as minor groove binders bind and stabilize helical DNA, and have been exploited as probes within the limited temperature range. By increasing the Tm, shorter primers and probes can function within DFA temperature range. For PCR temperature ranges, an example of this approach is the use of minor groove binding agents. Many other classes of agents, including those which bind to both single stranded and double stranded DNA, are contemplated as in the example below.

```
                                                    (SEQ ID NO: 11)
        ┌──5'-GGCTCTGAGGGGCCATA
       *│
        └──CCGAGACTCCCCGGTATCGATCGTAGCTAG ... 5'
```

As shown above, the primer or probe has a covalently linked moiety (labeled as "*") that binds to adjacent DNA and increases the primer/probe Tm. The stabilizing moiety can bind to either ds or ssDNA.

In a further embodiment, oligonucleotide backbone or base modifications that increase Tm can also be utilized to move primer/prove Tms into the DFA range without increasing oligonucleotide length.

Such modifications include but are not limited to LNA, PNA, dithiophospate linkages, 2' sugar modification such as 2'-O-Methyl, 2'-fluoro, base modifications such as 5-halopyridines, 5-methyl pyrimidines, bases which make additional hydrogen bonds, other purine base modifications such as super G, 2-amino purine, and the like.

iii. DFA Probe Technology—FRET Probes

Figure 8:
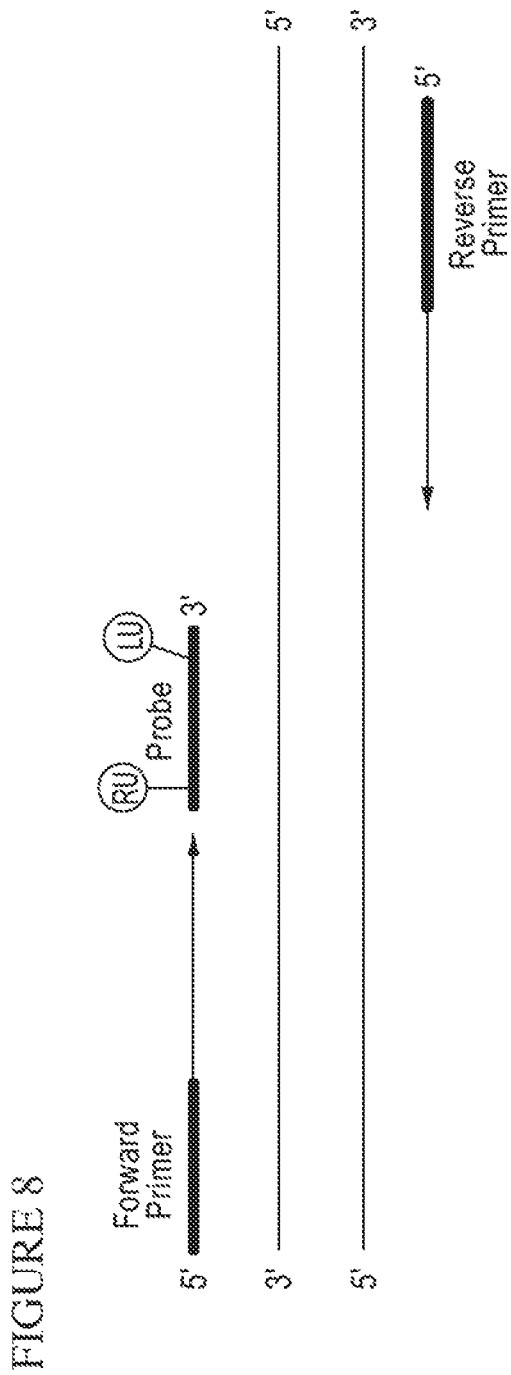
FIG. 8 depicts cleaved probe technology in an embodiment where bathophenanthroline-RU II complexes are used as label molecules.

In another embodiment of cleaved probe technology, depicted in FIG. 8, bathophenanthroline-RU II complexes are used as label molecules. These complexes can be part of an interactive pair of label molecules allowing energy transfers from suitable energy donor molecules to the Ru complex. Because the efficiency of the energy transfer is highly dependent on the distance between the donor and acceptor molecules, such energy transfer systems are useful in studying molecule interactions.

A suitable class of acceptor molecules for use as the Ru complexes is the lumazine chromophore group of molecules. Using such a combination, energy transfers may be detected between the Ru bathophenanthroline complex and the lumazine chromophores where the Ru complex is located at a suitable distance from the lumazine chromophore. When used in conjunction with polymerase cleaving technology, wherein one of the two labels is cleaved from the probe, a change in luminescence may be detected which is useful in determining whether amplification of the target sequence has been achieved.

Figure 9:
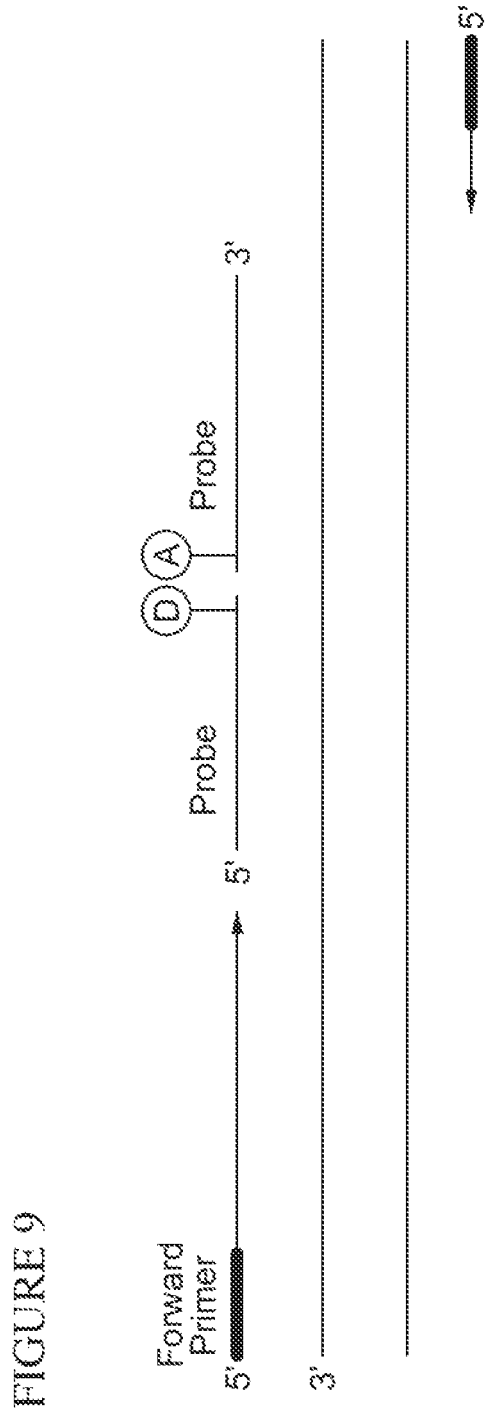
FIG. 9 depicts a Dual Hybridization Probe and Primer combination.

FIG. 9 depicts a Dual Hybridization Probe and Primer combination. This embodiment comprises two sequence-specific oligonucleotide probes in addition to two sequence specific primers. The probes comprise pairs of dyes that can engage in fluorescence resonance energy transfer. (FRET), with a donor dye attached to one probe and an acceptor dye attached to the other probe, with both the donor dye and the acceptor dye located such that when the probes are attached to the target sequence, they are sufficiently proximate to each other to engage in FRET. Both the probes and the primers meet the temperature requirements for XCR.

Figure 10:
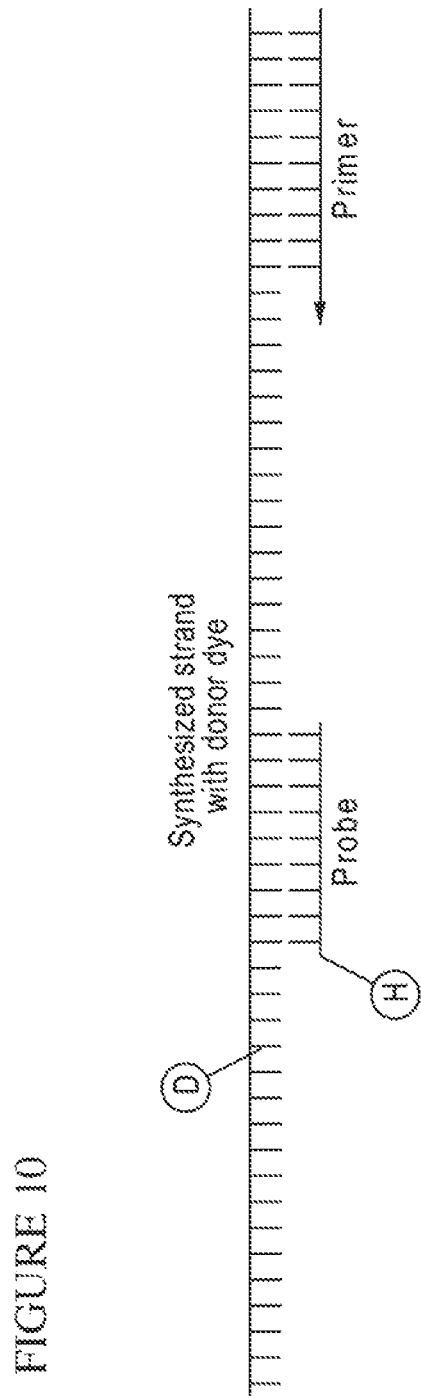
FIG. 10 depicts a primer/probe combination capable of engaging in FRET.

FIG. 10 depicts a primer/probe combination capable of engaging in FRET. A sequence-specific oligonucleotide primer and a sequence-specific oligonucleotide probe are designed to bind to adjacent sequences of the target, usually with the probe complementary to the strand formed by the primer, such that the probe anneals to the complementary strand synthesized from the extended labeled primer.

The following are examples of sequence designs for primer/probe combinations capable of engaging in FRET. The following example is in Ebola.

```
Sequence of double stranded Ebola DNA
                                (SEQ ID NOs: 12 and 61)
3781 ACATTTCGGCAAAGGATTTGAGAAACATTATGTATGATCACTTGC
     CTGGTTTTGGAACTGTGTAAAGCCGTTTCCTAAACTCTTTGTAATACATA
     CTAGTGAACGGACCAAAACCTTGAC
3841 CTTTCCACCAATTAGTACAAGTGATTTGTAAATTGGGAAAAGATA
     GCAACTCATTGGACAGAAAGGTGGTTAATCATGTTCACTAAACATTTAAC
     CCTTTTCTATCGTTGAGTAACCTGT
3901 TCATTCATGCTGAGTTCCAGGCCAGCCTGGCTGAAGGAGACTCTC
     CTCAATGTGCCCTAAAGTAAGTACGACTCAAGGTCCGGTCGGACCGACTT
     CCTCTGAGAGGAGTTACACGGGATT Foward Primer (SEQ ID NO: 13):
EbolaZFxcr
ATCACTTGCCTGGTTTTGGAACTGCTTT (-Q670) CCACC Reverse Primer (SEQ ID NO: 14):
EbolaZRxcr
CCTTCAGCCAGGCTGGCCT (-Ca1610) GGAACT Probe (SEQ ID NO: 15):
EbolaZXxcr
FAM-TACAAGTGATTTGTAAATTGGGAAA-GATAGCAACTCATTGGACAT
CATTCATGC-FAM
```

Designing assays containing probes and primers of these lengths yielded unexpected results in that it was generally thought that probes and primers of these lengths could not be designed to possess Tm's within the narrow ranges of the Tm of the target sequence required for DFA. However, it has been found that probes and primers with adequate Tm ranges for DFA can be readily designed.

EXAMPLES

Example 1 Control Test

The following probes and primers were created to be used in conjunction with DFA to amplify a control target sequence.

```
Target Sequence (SEQ ID NO: 16):
CCATTGCCATATTTGGTTATCAGGTATCTGTTAGAGGGGCTAAAGCTAAC
CCACCAATTCCTGTGCCAGAGSAATAAAATTCCCATCGCAATTCCTCTGT
GAGCACTGAAATAGGGCGGTGCATGAACAATAGCCGGTAGGTATGTCAGA
AAACCTCCAATGCCAAACATTACTCCTTGACTCAATGTTTCCTGTGCCCA
CGATGCGCTTATTAGACCCATGGCCATCAAAAGTGACCCGAGCACCATCG
TTTGTTGGATTGAAAAGAAGTGCTGTAGTACGTTATTACCGATG Foward Primer Sequence (SEQ ID NO: 17):
ATTGCCATCCATATTTGGTTATCAGGTATCTCGTTAGAGGGGCTAAAGCT
AACCCACCATTCC Reverse Primer Sequence (SEQ ID NO: 18):
GGTAATAACGTACTACATCAGCACTTCTTTTCAATCCAACGATGGTGCTG
GGTCACT Probe Sequence (SEQ ID NO: 19):
BHQ1-ACCTCCAATGCCAAACATTACTCCTTGACTCAATGT(T-FAM)
TCCTGTGCCCACGATGCGCTTATTAGACCCATGGCC-Phos
```

Target sequence Tm: 88.00° C.
Forward Primer Tm: 80.04° C.
Reverse Primer Tm: 80.07° C.
Probe Tm: 84.07° C.

Example 2 Flu Mat A Test

The following probe and primer assay design was created to be used in conjunction with DFA to test for Flu mat A:

```
Target Sequence (SEQ ID NO: 20):
GAGTGAGCGAGGACTGCAGCGTAGACGCTTTGTCCAAAATGCCCTNAATG
GGAATGGGGATCCAATAACATGGACAGAGCAGTTAAACTGTATAGGAAGC
```

```
-continued
TTAAGGGATAACGTTCCATGGGGCCAAAGAAATAGCACTCAGTTATTVTG
CTGGTGCACTTGCCAGTTGCATGGGCCTCATATACAACAGGATGGGGCT
GTGACCACNGAAGCNGCATTGCCTNGTATGTGCAACNTGTGAACAGATT
GCTGACTCCCAGCATAGGTCTCATAGGCAATGGTNACAACAACCAATCCA
TTAATAAGACATGAGAACAGAATGGTTCTGGCCAGCACTACAGCTAAGGC
TATGGAGCAAATGGC Foward Primer Sequence (SEQ ID NO: 21):
GTGAGCGAGGACTGCAGCGTAGACGCTTTGTCCAAAATGCC Reverse Primer Sequence (SEQ ID NO: 22):
GCCATTTGCTCCATAGCCTTAGCTGTAGTGCTGGCCAGAACCATTCTGTT
CTCATGTCTTATTAAT Probe sequence (SEQ ID NO: 23):
BHQ1-AGCACTCAGTTATTCTGCTGGTGCAC(T-FAM)
TGCCAGTTGCATGGGCCTCATATACAACAGGATGGGGGCT-Phos
```

Target sequence Tm: 89.4° C.
Forward Primer Tm: 79.9° C.
Reverse Primer Tm: 80.1° C.
Probe Tm: 85° C.

Example 3 S Aurues Nuc Gene Test

The following probe and primer assay design was created to be used in conjunction with DFA to test for S Aurues Nuc Gene:

```
Target Sequence (SEQ ID NO: 24):
AGCAAGTGCATTTACGAAAAAAATGGTAGAAAATGCAAAGAAAATTGAAG
TCGAGTTTGACAAAGGCCAAAGAACTGATAAATATGGACGTGGCTTAGCG
TATATTTATGCTGATGGAAAAATGGTAAACGAAGCTTTAGTTCGTCAAGG
CTTGGCTAAAGTTGCTTATGTTTATAAACCTAACAATACACATGAACAAC
TTTTAAGAAAAAGTGAAGCACAAGCGAAAAAAGAGAAATTAAATATTTGG
AGCG Forward Primer sequence (SEQ ID NO: 25):
AGCAAGTGCATTTACGAAAAAAATGGTAGAAAATGCAAAGAAAATTGAAG
TCGAGT Reverse Primer Sequence (SEQ ID NO: 26):
CGCTCCAAATATTTAATTTCTCTTTTTTTGCTTGTGCTTCACTTTTTCTT
AAAAGTTGTTCATGTGTATTGTTAGGT Probe sequence (SEQ ID NO: 27):
5'BHQ1-
ATGGACGTGGCTTAGCGTATA(T)TTATGCTGATGGAAAAATGGTAAACG
AAGCTTTAGTTCGTCAAGGCTTGGCTAAAGTTGCT-Phosphate
(T) = FAM - T Probe sequence (SEQ ID NO: 28):
BHQ1-AGCACTCAGTTATTCTGCTGGTGCAC(T-FAM)
TGCCAGTTGCATGGGCCTCATATACAACAGGATGGGGGCT-Phos
```

Target sequence Tm: 83° C.
Forward Primer Tm: 76.76° C.
Reverse Primer Tm: 76.76° C.
Probe Tm: 82° C.

Example 4 Primer/Primer XCR Detection Chemistry

Observation from extant probe detection chemistry, such as HybBeacon and HyGlow probes, show that the native folding of probes into tight secondary structures and the accompanying relative hydrophobicity of fluorescent dyes allows these fluorescent moieties to come into close proximity if not actual contact with one another. This is believed to occur from a general entropically favored configuration for the folded oligonucleotides and their attached dyes.

XCR has demonstrated its ability to amplify DNA or RNA templates at nearly 10× the speed of traditional PCR technologies. One substantial limitation to performing amplifications at those speeds is the need to incorporate a probe based detection during the amplification protocol. The primary source of the additional time required is the need for the hybridization of the probe, and in the case of 5' nuclease XCR probes, the additional time required for the probe to be cleaved to release quenching of the dye from its quencher.

The following describes a method of detecting fluorescence in real time amplification that takes advantage of the HybBeacon and HyGlow technologies, where fluorescence quenching is released by the binding of the oligonucleotide to its complement template.

According to this design, in lieu of the fluorescent oligonucleotide being a probe, the fluorescent molecules are the primers used to produce the amplification.

Figure 11:
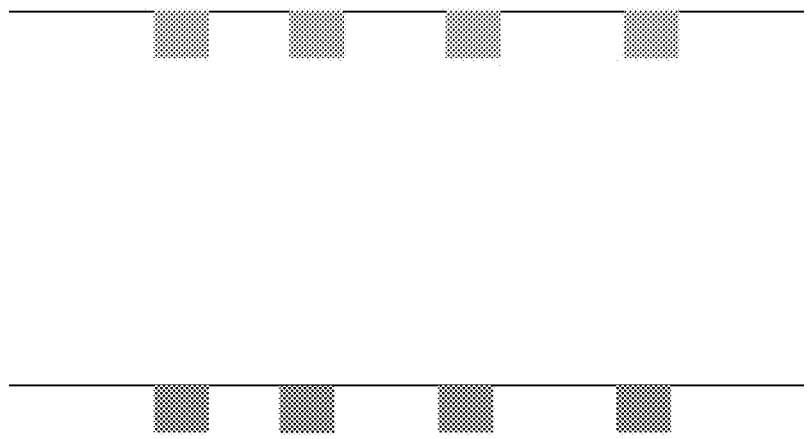
FIG. 11 illustrating forward (top) and reverse (bottom) primers with dye (squares) spaced approximately 6-9 nucleotides apart along the length of the primers, but with sufficient nucleotides left without dye on the 3' end. When the primers bind to their complement, fluorescence quenching is released and thus a detectable signal is created FIG. 12 illustrating quenched forward primer-dimer complex (top), quenched reverse primer-dimer complex (middle), and primer-dimer complex formed from the binding together of the forward and reverse primers (bottom), which is detectable via FRET signal. Squares represent dyes.

The primary advantage being that additional time to allow the fluorescent probe to bind is not required, as the primers are inherently annealed and 'streched' out on the template thus releasing the fluorescence quenching upon initiation of the priming complex. See FIG. 11, illustrating forward and reverse primers with dye spaced approximately 6-9 nucleotides apart along the length of the primers, but with sufficient nucleotides left without dye on the 3' end. When the primers bind to their complement, fluorescence quenching is released and thus a detectable signal is created.

The fluorescent primers serve several purposes in this design. First, two fluorescent signals are generated, one for the forward primer binding to the appropriate template and one for the reverse primer binding to the opposite strand template.

Should a primer form an extension product, primer-dimer, with another like primer then dyes on the primer should be in close enough proximity to prevent the release of quenching and thus remain quenched and produce no fluorescent signal from such primer-dimer complexes.

Should the two differently labeled primers form a primer-dimer complex, their quenching will not be relaxed, but rather a FRET complex will be formed, and the signal indicating the formation of the primer-dimer complex will be monitorable by excitation at the higher energy wavelength with emission at the lower energy wavelength (a standard FRET signal). See FIG. 12, illustrating quenched forward primer-dimer complex, quenched reverse primer-dimer complex, and primer-dimer complex formed from the binding together of the forward and reverse primers, which is detectable via FRET signal.

Figure 13:
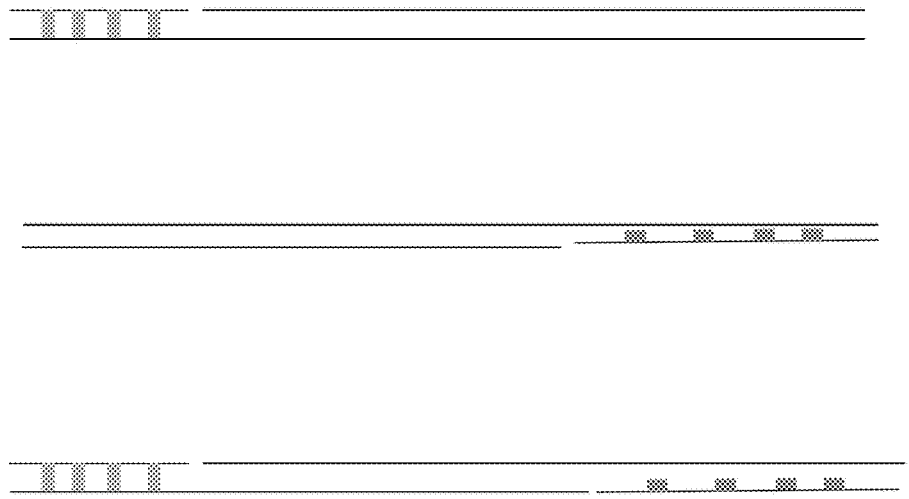
FIG. 13 illustrating forward primer template formation signal (top), and reverse primer template formation signal (middle), and signal generated when both the forward and reverse primers produce the targeted template (bottom). Squares represent dye.

Under certain circumstances, where template dependent non-specific product is made, it may be possible for a single primer to initiate the priming of a template. These products will produce single fluorescent dye signals. See FIG. 13, illustrating forward primer template formation signal, and reverse primer template formation signal, and signal generated when both the forward and reverse primers produce the targeted template.

Figure 14:
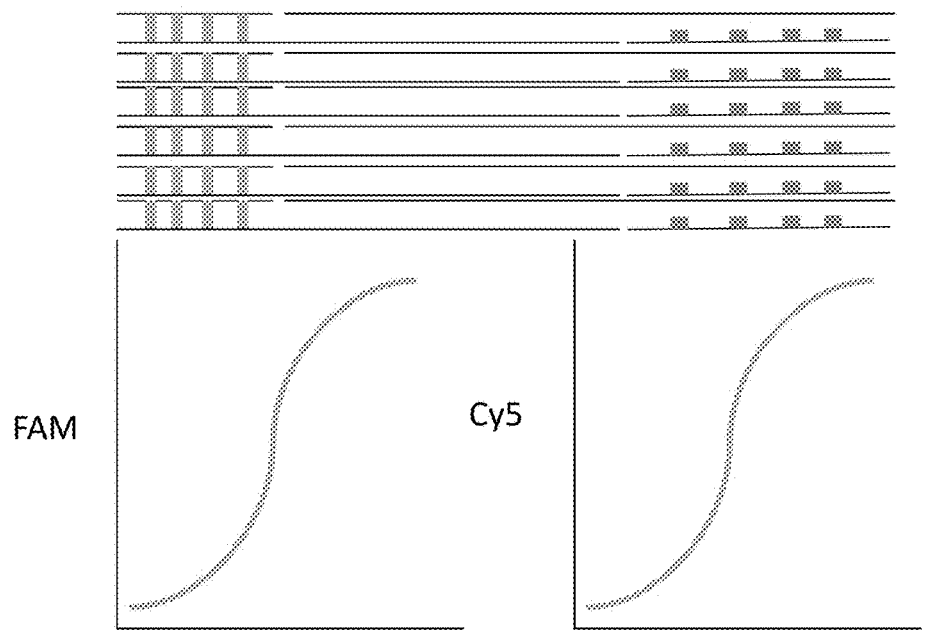
FIG. 14 illustrating that correct products with both dye labeled primers will show the formation of fluorescent signal from both distinct dyes with equal reaction formation efficiency, as they will be linked directly to one another in the formation of amplification product and could be monitored in two fluorescent channels simultaneously. Forward primer signal on left and reverse primer signal on the right.

Whereas, correct products with both dye labeled primers will show the formation of fluorescent signal from both distinct dyes with equal reaction formation efficiency as they will be linked directly to one another in the formation of amplification product and could be monitored in two fluorescent channels simultaneously. See FIG. 14.

Figure 15:
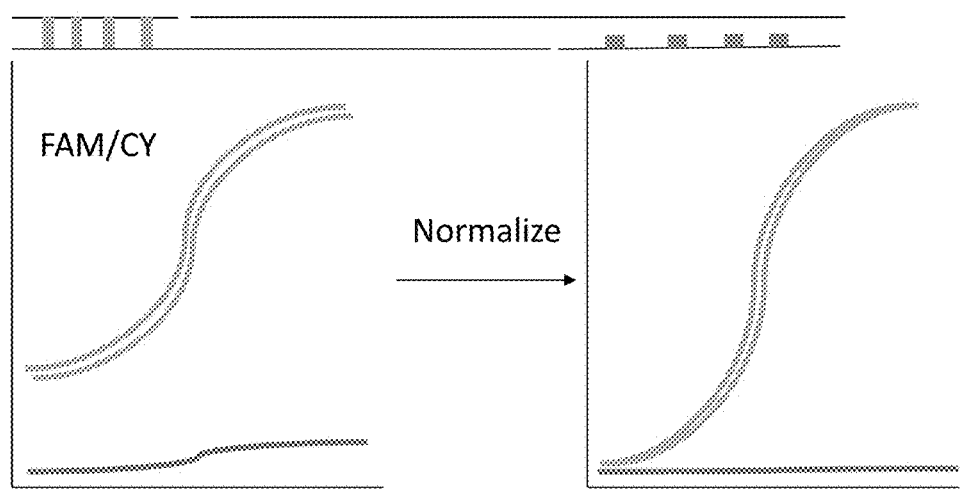
FIG. 15 illustrating a data evaluation advantage of the present disclosure design strategy is where amplified product is formed and both fluorescent signals are generated by the amplifying product. Any primer-dimer signals that result in FRET, as the like primers will be quenched, can be subtracted from the formed signals to enable a baseline normalization of the amplification signals. Forward and reverse primer signals forming sigmoidal curve. Primer-dimer signal to be subtracted is illustrated via line at the bottom of the graph.

Another data evaluation advantage of this design strategy is where amplified product is formed and both fluorescent signals are generated by the amplifying product. Any primer-dimer signals that result in FRET, as the like primers will be quenched, can be subtracted from the formed signals to enable a baseline normalization of the amplification signals. See FIG. 15.

Overall, the advantage of this technique is that it will not limit XCR speed during the amplification by no longer needing to wait for the probe to hybridize or for the probe to be cleaved.

In addition to XCR, this design is suitable for PCR assays as well; however, the reason that such a chemistry has not been implemented and it has been non-obvious is that PCR suffers from substantial non-specific product formation and the use of primers only, as in the case of double stranded DNA binding dyes like SYBR Green 1, have been largely ignored as suitable for diagnostic testing methodology.

The following illustrates a sequence configuration suitable for this method.

```
Exemplary Forward Primer with FAM Dyes highlighted
(SEQ ID NO: 29):
AGGGCGGTGCATGAACAATAGCCGGTAGGTATGTCAGAAAACCTCCAA 80.7° C. Tm Exemplary Reverse Primer position of RED dyes
highlighted (SEQ ID NO: 30):
ATGGCCATGGGTCTAATAAGCGCATCGTGGGCACAGGAA 80.8° C. Tm Exemplary Target Sequence (SEQ ID NO: 31):
AAGAGGGAAGAGGGGGAGGGCGGTGCATGAACAATAGCCGGTAGGTATGTCAGAA
AACCTCCAATGCCAAACATTACTCCTTGACTCAATGTTTCCTGTGCCCACGATGCGC
TTATTAGACCCATGGCCATCAAAAGTGACCCGAGCACCATCGTTTGTTGGATTGAAA
AGAAGTGCTGT 88.9° C. Tm
```

Example 5 Triplex Forming Region Probe Design

In another embodiment, the present disclosure provides a multiplex probe technology that is suited for use with DFA.

This embodiment minimizes the required number of oligos (e.g., primers and probes) by eliminating the need for the probes to participate in the amplification portion of the reaction.

Most current probe technology utilizes individual or multiple oligonucleotides to probe for the amplified sequence. The oligonucleotide probes bind to the sequence of interest in the course of the DNA amplification.

In contrast, the current disclosure uses triplex forming regions (TFR) appended to sequence specific primers. This disclosure then uses a triplex forming oligonucleotide probe designed to interact with each specific product at the TFR to produce a unique color of fluorescence based on the particular product formed. This reduces the number of oligonucleotides present in the reaction.

The triplex forming probe does not participate in the amplification reaction and hence does not slow the reaction down in the way existing probe technology has a tendency to do.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

The practice of the present disclosure will employ, unless otherwise indicated, conventional techniques of molecular biology, microbiology, and recombinant DNA techniques as explained fully in the literature, as well as the methods disclosed in U.S. Pat. No. 7,838,235, incorporated herein by reference in its entirety.

In one embodiment, a triplex forming oligonucleotide probe based detection chemistry for nucleic acid amplification products is utilized. According to this method, a triplex forming primer is synthesized according to the following method.

An artificial sequence triplex forming region (TFR) is added to the designed oligonucleotide to create the triplex forming primer.

As used herein, a triplex forming region, or TFR, refers to particular DNA sequences that lend themselves to Hoogsteen, or triplex base pairing, in that a third strand of DNA binds to the double stranded TFR to form a triple stranded length of DNA, known as a triplex.

The following are illustrative examples of sequences that form triplex forming regions:

```
                                              (SEQ ID NO: 32)
5'-GTGTGGGAAGAGGGGGAXGAGGGGGAGGAGC-3'

(SEQ ID NO: 33)
3'-CACACCCCTTCTCCCTXCTCCCCTCCGTCG-5'

(SEQ ID NO: 34)
5'-GTGTGGGAAGAGGGGGAXGAGGGGGAGGAGC-3'

(SEQ ID NO: 35)
3'-CACACCCCTTCTCCCTXCTCCCCTCCGTCG-5'
```

In one embodiment, the TFR is located on the 5' end of the designed primer.

In an alternative embodiment, the TFR is located proximate to the 5' end of the designed primer.

In another embodiment, the TFR is located at any location internal to the designed primer.

In another embodiment, the TFR is located on the 3' end of the designed primer.

In another embodiment, the TFR is located proximate to the 3' end of the designed primer.

The triplex forming primer can be a segment of DNA or RNA that is complementary to a given DNA sequence and that is needed to initiate replication by DNA polymerase.

The triplex forming oligonucleotide may comprise a Triplex Forming Oligonucleotide probe (TFO probe). The TFO probe can be complexed to an appropriate sequence triplex forming region of double stranded nucleic-acid sequence and thus, when the TFO probe is labeled in some manner, as with a fluorophore, the TFO probe can be used to identify any nucleic-acid sequences.

In one embodiment, the primer comprising a Triplex Forming Region (TFR primer) may also possess a fluorescent dye.

Figure 16:
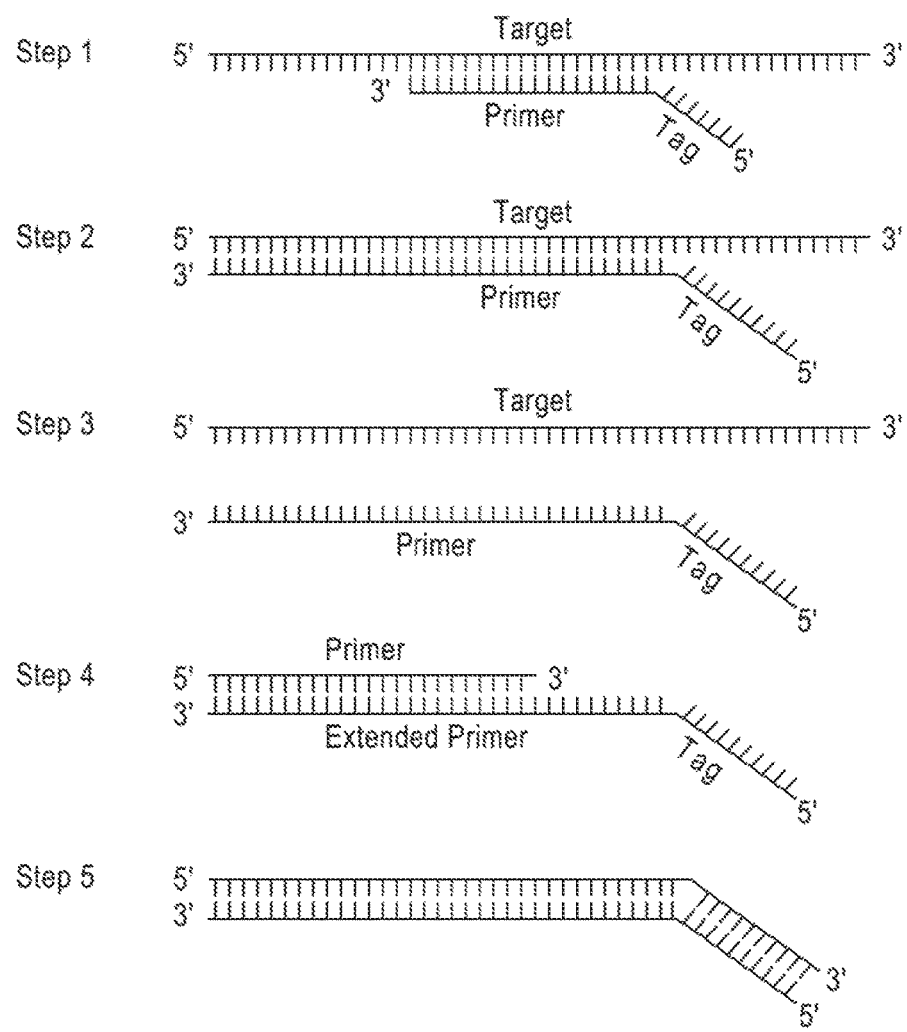
FIG. 16 illustrates that the TFR primer participates in the amplification of the target sequence, creating strands of triplex forming DNA along the length of and appended to the target sequence.

As depicted in FIG. 16, the TFR primer participates in the amplification of the target sequence, creating strands of triplex forming DNA along the length of and appended to the target sequence.

Step 1 depicts the single strands of the denatured DNA of the target sequence, bonded to the oligonucleotide primer.

The oligonucleotide primer comprises a tag end sequence that does not match the target sequence. The tag end sequence comprises one or more triplex forming sequences.

Step 2 depicts the extension phase of the amplification process. During this phase, the primer is extended towards its 3' end to create a target for the next cycle.

Step 3 depicts the extended primer denatured from the target.

Step 4 depicts a primer with no tag annealed to the extended TFR primer.

Step 5 depicts the extension phase of the primer with no tag to create double stranded DNA sequence with a Triplex Forming Region.

The following detection method may then be employed to determine whether the TFO probe has bonded with the double stranded Triplex Forming Region of the amplified DNA, indicating that the DNA possesses the sequence of interest.

As depicted in FIG. 16, a triplex forming oligonucleotide probe is created in the following manner. A single stranded TFO is designed to bind to the Triplex Forming Region in the target sequence that was created during the amplification process. A dye capable of engaging in fluorescence energy transfer (FRET) is attached to the triplex TFO probe. In this instance, the dye is the donor dye. The following are two examples of a single stranded DNA that forms a triplex with a double stranded DNA with a TFR:

```
                                              (SEQ ID NO: 36)
  5'-GGAGGGGGAGAAGGGAGAAGGG-3'

(SEQ ID NO: 37)
  3'-CCTCCCCCTCTTCCCTCTTCCC-5'

(SEQ ID NO: 38)
  5'-GGTGGGGGTGTTGGGTGTTGGG-3'TFO (SEQ ID NO: 39)
  3'-GGGTTGTGGGTTGTGGGGTGG-5'TFO (SEQ ID NO: 40)
  5'-GTGTGGGAAGAGGGGGAXGAGGGGGAGGAGC-3'

(SEQ ID NO: 41)
  3'-CACACCCCTTCTCCCTXCTCCCCTCCGTCG-5'
```

Figure 17:
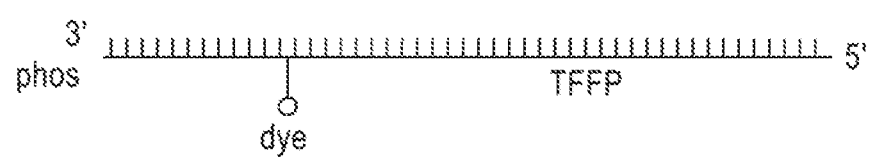
FIG. 17 illustrates a triplex forming oligonucleotide probe with the 3' end of the TFO probe being capped.

As depicted in FIG. 17, the 3' end of the TFO probe is capped with a phosphate to prevent the TFO probe from participating in the amplification process. The TFO probe may also be capped by a fluorescent dye, a non-extendable linker, or any other suitable atom or molecule known to those of ordinary skill in the art to prevent oligonucleotide extension during amplification reactions. The donor dye may be attached at or proximate to the 3' end of the probe. The donor dye may also be attached at or proximate to the 5' end of the TFO probe. The donor dye may also be attached anywhere between the 5' end and the 3' end of the TFO probe. When a dye is attached to the TFO probe, it comprises a triplex forming fluorescent probe (TFFP).

Figure 18:
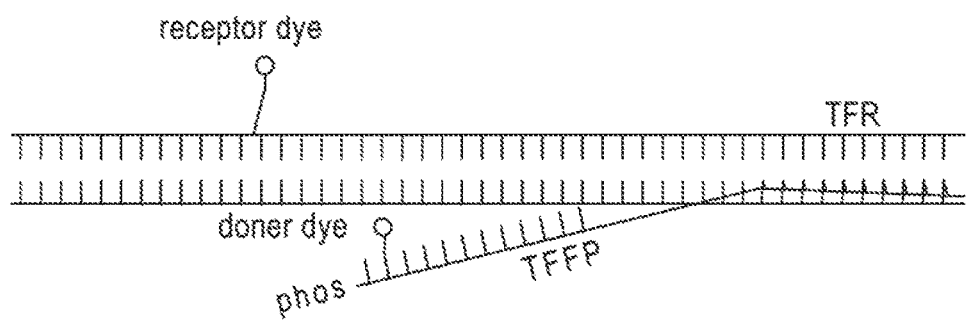
FIG. 18 depicts a double stranded DNA sequence comprising a Triplex Forming Region. The double stranded DNA sequence possesses a receptor dye. The TFR of the TFFP attaches to the Triplex Forming Region of the double stranded DNA.

FIG. 18 depicts a double stranded DNA sequence comprising a Triplex Forming Region. The double stranded DNA sequence possesses a receptor dye. The TFR of the TFFP attaches to the Triplex Forming Region of the double stranded DNA.

In one embodiment, the TFFP anneals to the amplified DNA only when the temperature of the reaction is at or below the annealing temperature of the primers. Thus, the triplex forming fluorescent probe does not participate in the reaction. When the TFFP bonds to the amplified sequence, and a light is shone on the product, the donor dye on the TFFP resonates. As the donor dye resonates, it transfers energy to a receptor dye located on the double stranded DNA, causing the receptor dye to fluoresce at a particular wavelength, emitting light of a color that corresponds to that wavelength. This indicates that the sequence of interest was present in the test sample and has been amplified.

In an alternative embodiment, the receptor dye is attached to the TFFP and the donor dye is attached to the amplified double stranded DNA product. In this embodiment, the acceptor dye fluoresces when the sequence of interest has been amplified.

In another embodiment, a plurality of primers may be used, with each primer designed to bind to and specifically amplify a different sequence of interest. Each primer has a different acceptor dye attached to it such that each acceptor dye fluoresces at a different wavelength. The triplex forming fluorescent probe will bind to the Triplex Forming Region of the amplified product. A donor dye attached to the triplex forming probe will cause the acceptor dye on the amplified product to fluoresce a certain color, depending on which product has been amplified. In this manner, a plurality of different sequences may be tested for at once. This embodiment would allow a plurality of different potential sequences of interest to be tested for in one reaction vessel. Testing for a plurality of different potential sequences of interest in one reaction vessel is known as multiplexing.

In an alternative embodiment of a multiplex probe combination, the acceptor dye may be attached to the TFFP and the donor dye can be attached amplified double stranded DNA product. In this embodiment, each primer would have a different colored donor dye, such that the acceptor dye, attached to the TFO probe, will fluoresce at a different color, depending on which primer has amplified the sequence of interest.

In another embodiment, the TFO probe is designed to anneal at approximately the same temperature, or at a slightly higher or lower temperature than the Tm of the primers. This embodiment allows for the reading of amplification results in real time.

Example 6 Triplex Forming Region Probe Design with Naturally Occurring TFRs

Another embodiment takes advantage of naturally occurring triplex forming regions (TFR) that are located within or adjacent the sequence of interest itself. The following are examples of naturally occurring TFR sequences in double stranded DNA.

```
                              (SEQ ID NO: 42)
  5'TTTTTTCCCGTCC 3'

(SEQ ID NO: 43)
  3'AAAAAGGGCAGG 5'

(SEQ ID NO: 44)
  5'GGCGAGGGGGAGCGGG 3'

(SEQ ID NO: 45)
  3'CCGCTCCCCCCTCGCCC 5'

(SEQ ID NO: 46)
  5'GGAGGTGGGGGAG 3'

(SEQ ID NO: 47)
  3'CCTCCACCCCCTC 5'
```

5'GGAGGTGGGGGAG 3' (SEQ ID NO: 48)

3'CCTCCACCCCCTC 5' (SEQ ID NO: 49)

5'GGAGAAGGTGAGGAAGAAGAAGAGGAAGAA 3' (SEQ ID NO: 78)

In this embodiment, the primers are designed to bond with the naturally occurring triplex forming regions as well as with the sequence of interest.

In this way, the triplex forming region of the DNA is amplified to detectable levels as the sequence of interest is amplified. The primer has a receptor dye attached to it. The triplex forming probe is created having a sequence complementary to the naturally occurring sequence of interest.

In another embodiment of a method of multiplexing, each set of primers designed to test for a particular sequence of interest comprises its own unique TFR base pair sequence in addition to its own unique color dye. In one embodiment, the dye would be a donor dye. A plurality of TFO probes is then designed, each set of which comprises a TFR to match a particular TFR of one of the amplified products. Each set of probes also comprises its own unique acceptor dye color. Which product is amplified determines which probe will bond with it. Which probe attaches to the amplified product, and hence, which sequence of interest exists in the sample, is determined by the color of the probe's fluorescence when it undergoes FRET with the dye of the TFO probe.

In another embodiment, the detection method may comprise the use of specialty DNA binding dyes that bind preferentially to triplex DNA structures. In one embodiment, the dye comprises Thiazole Orange. In another embodiment, the dye comprises Cyanine 40 dye. In addition to the dyes set forth herein, any other dyes that bind preferentially to triplex DNA structures, known by those of ordinary skill in the art, may be used. These triplex binding dyes may be used in combination with dye labeled TFRs, either on the primers or internal to the product itself, to produce a FRET based signal that could also indicate the presence of specifically formed target sequence(s).

Figure 19:
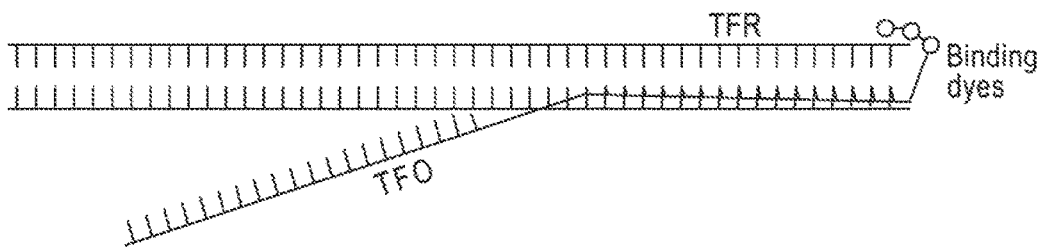
FIG. 19 illustrates that the binding dyes, constrained by covalent attachment to a particular location on the TFO probe, in this instance, the end of the TFO probe, can only bind to hybridized DNA structures when the TFO probe is bound and thus, puts the TFO probe in proximity to the dye attached to the amplified sequence of interest. Thus, a fluorescent signal indicates that amplification has occurred.

An alternative method involves TFO probe coupling to DNA binding dyes. These would include, without limitation: Sybr Green 1; Sybr Gold; Eva Green; LightCycler Green I; LightCycler Green II; Toto/Yoyo/Toyo; and other DNA binding dyes that bind to hybridized DNA structures known to those of ordinary skill in the art. As depicted in FIG. 19, the binding dyes, constrained by covalent attachment to a particular location on the TFO probe, in this instance, the end of the TFO probe, can only bind to hybridized DNA structures when the TFO probe is bound and thus, puts the TFO probe in proximity to the dye attached to the amplified sequence of interest. Thus, a fluorescent signal indicates that amplification has occurred.

In yet another embodiment, Cy2 or other quadruplex binding dyes known to those of ordinary skill in the art may be used.

In another embodiment, the TFO probe may be synthesized with a fluorescent dye and quencher located anywhere along its length. As depicted in FIG. 20, this embodiment utilizes a hairpin dye and quencher configuration. Upon the binding of the TFO probe to the sequence of interest, the hairpin structure of the probe is eliminated, with the result that the quencher becomes sufficiently distal from the dye that it is no longer able to suppress the dye's fluorescence. This results in a fluorescence of a certain color being emitted if the sequence of interest has been amplified. The specific fluorescent signal change is irrelevant so long as it is distinguishable from that of any other product in the reaction mix. The total number of reactions that can be detected can be distinguished only depends on the instrument platform that the reactions are being performed on.

Figure 21:
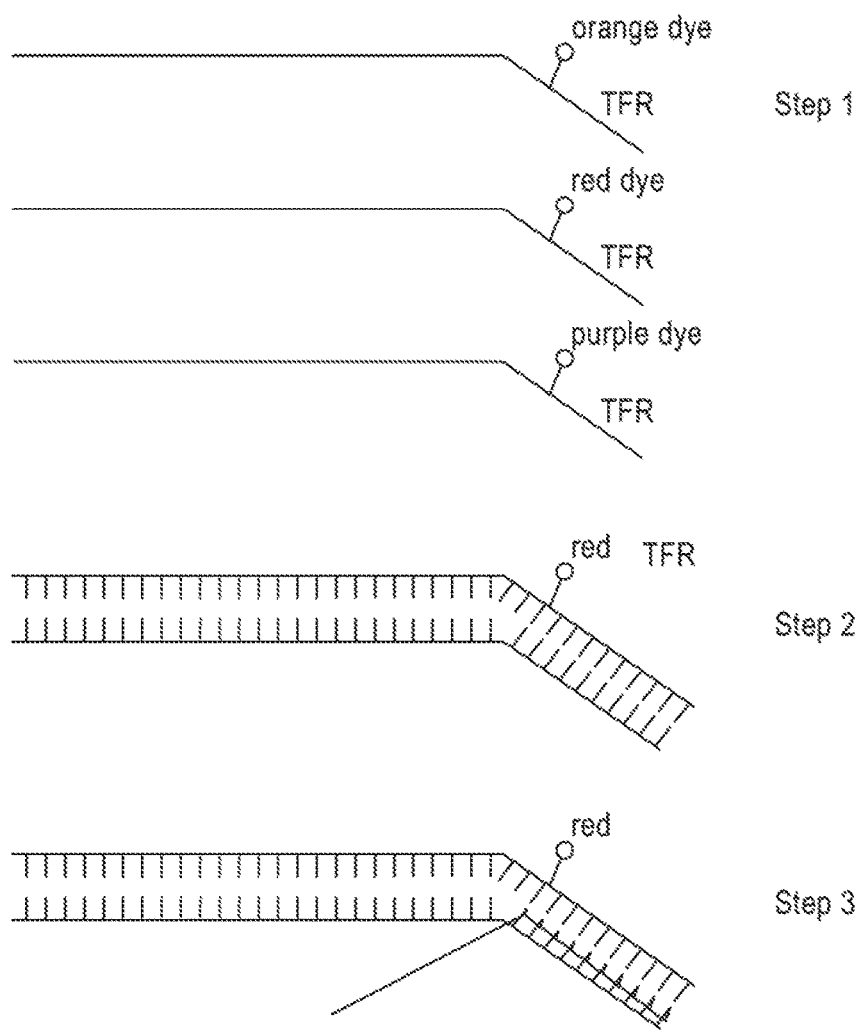
FIG. 21 illustrates that two or more primers with the same TFR sequence may be used along with TFR primers that comprise a sequence complementary to the TFR sequence.

In another embodiment, depicted in FIG. 21, two or more primers with the same TFR sequence may be used along with TFR primers that comprise a sequence complementary to the TFR sequence. FIG. 21, depicts three TFR primers, each with a different color dye. In step 2, the primer comprising the red dye has bound to the sequence of interest and amplified. In step 3, the TFR primer has bound to the TFR in the presence of a binding dye that binds preferentially to a triplex. Such a binding dye may comprise Thiazole Orange, Cyan 40, or any other triplex binding dye known to those of ordinary skill in the art. The binding dye engages in FRET with the attached fluorophore, indicating that the sequence complementary to the primer comprising the red dye has been amplified.

Figure 22:
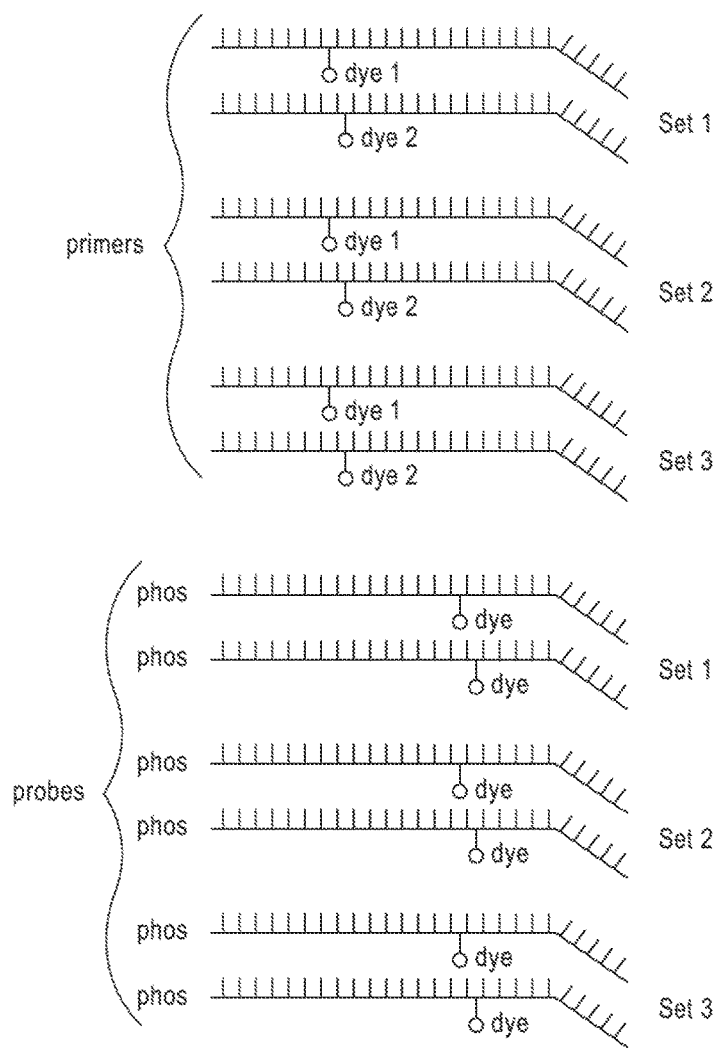
FIG. 22 depicts an embodiment wherein six primers are divided into three sets of two each.

In an alternative embodiment, the products may be distinguished by color, melting temperature, or a combination of both color and melting temperature of the triplex products. FIG. 22 depicts an embodiment wherein six primers are divided into three sets of two each. Each set of two primers comprises the same TFR sequence and the three sets each comprise three different TFR sequences such that each of the three sets of primers are distinguishable from the other two by virtue of having a different melting temperatures. The two TFR sharing primers within each set each has a different color dye. The method also comprises using three sets of probes comprising a sequence that binds the TFR of one of the pairs of primers. The products would then be distinguishable based its unique combinations of melting temperature and color. These various methods of distinguishing product would enable the use of Triplex DNA formation in the detection of amplified product as quantitative, genotyping, or simply target detection.

Figure 23:
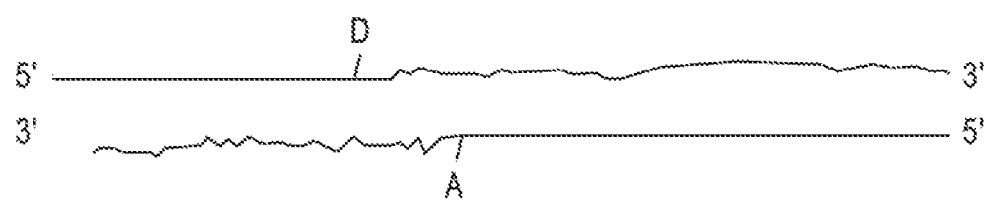
FIG. 23 the donor dye is attached near the 3' end of the first primer, while the acceptor dye is attached near the 3' end of the second primer.
Figure 24:
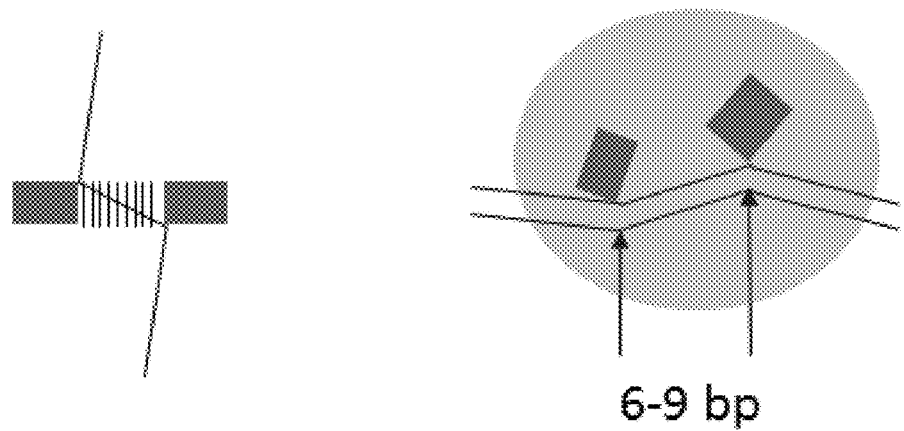
FIG. 24 generic structure illustrating binding dyes in solution on the left and attached to a nucleotide on the right.

The following is an alternative embodiment of primer and probe technology designed to take advantage of the unique characteristics of DFA. In this embodiment, each primer of a pair of primers is labeled with a dye that can engage in fluorescence resonance energy transfer (FRET). As depicted in FIG. 23, the donor dye is attached near the 3' end of the first primer, while the acceptor dye is attached near the 3' end of the second primer. At the annealing step, the primers hybridize to their target sequences in a near tail-to-tail arrangement brings the dyes into sufficient proximity, for FRET to occur. The amount of acceptor fluorescence is proportional to the amount of DFA product present.

The assay kits of the present disclosure for amplifying and/or detecting a target sequence of a DNA sample can include: i) the primers and probes described herein, and ii) buffer, dNTP's, andenzymes. Such reactants are present in sufficient quantities to conduct a plurality of assays.

Example 7 Further Triplex Forming Region Probe Designs

Triplex forming oligonucleotides provide a unique method for the detection of amplification products from either PCR, XCR, RAMP, HDA, NEAR or any other amplification technology that results in large quantities of amplified double stranded DNA.

We have described the introduction of artificial TFRs either attached somewhere along the length of a primer. More interesting though, is the natural occurrence of triplex forming regions (TFRs), which is surprisingly abundant. For example, *Streptococcus agalactiae* with a 2 million base pair genome, has as many as 29 TFRs of 16 base pairs or longer. Such relatively high abundance of such TFRs makes it plausible to utilize such TFRs (either homopurine or homopyrimidine stretches) as potential diagnostic markers for the amplification of the desired nucleic acid.

One such example of a basic design of a triplex forming oligonucleotide for use in detection of amplified DNA is diagrammed below, where a set of primers suitable for use in DFA produce an amplification product that is both diagnostic for the target of choice and the sequence between the primers contains a triplex forming region (TFR) that can be suitably detected with a triplex forming oligonucleotides (TFO).

The TFO would bind to the amplified double stranded DNA at any point during the reaction where the complete double stranded extension has occurred through the TFR portion of the product.

Advantageously, such binding events can be monitored at many different stages of the amplification and thus will not, like other hybridization chemistries, obligate the real-time readout to occur at the lowest temperature of the reaction where the unextended single stranded DNA is exposed for probe binding.

One distinct advantage of being able to use higher temperatures for the fluorescent reads is that reactions can be sped up to maximal velocity with the commensurate advantage of not encouraging non-specific product formation by holding for extended times at relatively low reaction temperatures.

TFOs for use in Detection of Amplified Adenovirus:

```
                                                          (SEQ ID NO: 50)
Adenovirus XCR FORWARD:  CGTGAGCTCGTCTTCCAGGAGCCTGAT (SEQ ID NO: 51)
Adenovirus XCR REVERSE:  GTCTCCCGGTGCGTCGCCGT (SEQ ID NO: 52)
9001 CTGGGCATTGCGGGCCGAGACCGTGAGCTCGTCTTCCAGGAGCCTGATGAGCTCGGCGAT
     GACCCGTAACGCCCGGCTCTGGCACTCGAGCAGAAGGTCCTCGGACTACTCGAGCCGCTA 9061 GGTGGCGCGCACCTCGCGCTCGAAATCCCCGGGGGCCTCCTCTTCTTCCTCTTCTTCCAT
                                 3'  F-GGAGGAGAAGGAGAAGAAGGTA-Q
     CCACCGCGCGTGGAGCGCGAGCTTTAGGGGCCCCCGGAGGAGAAGAAGGAGAAGAAGGTA 9121 GACGACCTCTTCTTCTATTTCTTCCTCTGGGGCGGTGGTGGTGGCGGGGCCCGACGACG
     CTGCTGGAGAAGAAGATAAAGAAGGAGACCCCCGCCACCACCACCGCCCCGGGCTGCTGC 9181 ACGGCGACGCACCGGGAGACGGTCGACGAAGCGCTCGATCATCTCCCCGCGGCGGCGACG
     TGCCGCTGCGTGGCCCTCTGCCAGCTGCTTCGCGAGCTAGTAGAGGGGCGCCGCCGCTGC
```

The TFO probe that is bound within the longer adenovirus nucleotide of SEQ ID NO: 52 is designated SEQ ID NO: 53 and contains the 3' F and 5' Q labels.

Also, we know that we can use minor groove binders to make shorter TFOs and to stabilize their binding.

TFOs can also be used to genotype for sequence variations, as shown below.

The TFO hairpin probe that is bound within the longer adenovirus nucleotide of SEQ ID NO: 52 is designated SEQ ID NO: 54 and contains the complementary end bases that are able to form the hairpin structure when the probe is not bound do target.

Minor Groove Binder TFOs:

```
                                                          (SEQ ID NO: 50)
Adenovirus XCR FORWARD:  CGTGAGCTCGTCTTCCAGGAGCCTGAT (SEQ ID NO: 51)
Adenovirus XCR REVERSE:  GTCTCCCGGTGCGTCGCCGT (SEQ ID NO: 55)
TFOmgb:Q-mgb-GGAGGAGAAGGAGAAGAAGGTA-F (SEQ ID NO: 52)
9001 CTGGGCATTGCGGGCCGAGACCGTGAGCTCGTCTTCCAGGAGCCTGATGAGCTCGGCGAT
     GACCCGTAACGCCCGGCTCTGGCACTCGAGCAGAAGGTCCTCGGACTACTCGAGCCGCTA
```

```
9061 GGTGGCGCGCACCTCGCGCTCGAAATCCCCGGGGGCCTCCTCTTCTTCCTCTTCTTCCAT
                       3'-Q-mgb-GGAGGAGAAGGAGAAGAAGAAGGTA-F
             CCACCGCGCGTGGAGCGCGAGCTTTAGGGGCCCCCGGAGGAGAAGAAGGAGAAGAAGGTA 9121 GACGACCTCTTCTTCTATTTCTTCCTCTGGGGCGGTGGTGGTGGCGGGGCCCGACGACG
     CTGCTGGAGAAGAAGATAAAGAAGGAGACCCCCGCCACCACCACCGCCCCGGGCTGCTGC 9181 ACGGCGACGCACCGGGAGACGGTCGACGAAGCGCTCGATCATCTCCCCGCGGCGGCGACG
     TGCCGCTGCGTGGCCCTCTGCCAGCTGCTTCGCGAGCTAGTAGAGGGGCGCCGCCGCTGC
```

The TFO minor groove binder (mgb) probe that is bound within the longer adenovirus nucleotide of SEQ ID NO: 52 is designated SEQ ID NO: 55.

Dual MGB Binder TFOs:

These TFOs may be particularly useful when TFRs are short and there is a need for additional stability to allow the TFO to bind during the DFA thermal cycling conditions.

```
                                                      (SEQ ID NO: 50)
Adenovirus XCR FOR: CGTGAGCTCGTCTTCCAGGAGCCTGAT (SEQ ID NO: 51)
Adenovirus XCR REV: GTCTCCCGGTGCGTCGCCGT (SEQ ID NO: 56)
TFOmgb2:  Q-mgb-GGAGGAGAAGGAGAAGAAGAAGGTA-mgb-F (SEQ ID NO: 52)
9001 CTGGGCATTGCGGGCCGAGACCGTGAGCTCGTCTTCCAGGAGCCTGATGAGCTCGGCGAT
     GACCCGTAACGCCCGGCTCTGGCACTCGAGCAGAAGGTCCTCGGACTACTCGAGCCGCTA 9061 GGTGGCGCGCACCTCGCGCTCGAAATCCCCGGGGGCCTCCTCTTCTTCCTCTTCTTCCAT
                       3'-Q-mgb-GGAGGAGAAGGAGAAGAAGAAGGTA-mgb-F
     CCACCGCGCGTGGAGCGCGAGCTTTAGGGGCCCCCGGAGGAGAAGAAGGAGAAGAAGGTA 9121 GACGACCTCTTCTTCTATTTCTTCCTCTGGGGCGGTGGTGGTGGCGGGGCCCGACGACG
     CTGCTGGAGAAGAAGATAAAGAAGGAGACCCCCGCCACCACCACCGCCCCGGGCTGCTGC 9181 ACGGCGACGCACCGGGAGACGGTCGACGAAGCGCTCGATCATCTCCCCGCGGCGGCGACG
     TGCCGCTGCGTGGCCCTCTGCCAGCTGCTTCGCGAGCTAGTAGAGGGGCGCCGCCGCTGC
```

The TFO dual minor groove binder (mgb) probe that is bound within the longer adenovirus nucleotide of SEQ ID NO: 52 is designated SEQ ID NO: 56.

Genotyping with TFOs:

The present disclosure provides for methods of utilizing TFOs to perform genotyping.

```
                                                      (SEQ ID NO: 50)
Adenovirus XCR FOR: CGTGAGCTCGTCTTCCAGGAGCCTGAT (SEQ ID NO: 51)
Adenovirus XCR REV: GTCTCCCGGTGCGTCGCCGT (SEQ ID NO: 57)
TFOgenotype1: Q-GGAGGAGAAGGAGGAGAAGAAGGTA-F (SEQ ID NO: 58)
TFOgenotype2: Q-GGAGGAGAAGGAGAAGAAGAAGGTA-R
```

Genotype 1 Amplicon:

In embodiments, where the signal can be generated only with perfect matches to the TFO or with the hairpin forming TFO, could be used for melt curve analysis.

```
                                                      (SEQ ID NO: 52)
9001 CTGGGCATTGCGGGCCGAGACCGTGAGCTCGTCTTCCAGGAGCCTGATGAGCTCGGCGAT
     GACCCGTAACGCCCGGCTCTGGCACTCGAGCAGAAGGTCCTCGGACTACTCGAGCCGCTA

9061 GGTGGCGCGCACCTCGCGCTCGAAATCCCCGGGGGCCTCCTCTTCTTCCTCTTCTTCCAT
                       3'-Q-GGAGGAGAAGGAGAAGAAGAAGGTA-F
     CCACCGCGCGTGGAGCGCGAGCTTTAGGGGCCCCCGGAGGAGAAGAAGGAGAAGAAGGTA
```

-continued
```
9121 GACGACCTCTTCTTCTATTTCTTCCTCTGGGGGCGGTGGTGGTGGCGGGGCCCGACGACG
     CTGCTGGAGAAGAAGATAAAGAAGGAGACCCCCGCCACCACCACCGCCCCGGGCTGCTGC 9181 ACGGCGACGCACCGGGAGACGGTCGACGAAGCGCTCGATCATCTCCCCGCGGCGGCGACG
     TGCCGCTGCGTGGCCCTCTGCCAGCTGCTTCGCGAGCTAGTAGAGGGGCGCCGCCGCTGC
```

Genotype 2 Amplicon:
In embodiments, where the signal can be generated only with perfect matches to the TFO or with the hairpin forming TFO, could be used for melt curve analysis.

(SEQ ID NO: 52)
```
9001 CTGGGCATTGCGGGCCGAGACCGTGAGCTCGTCTTCCAGGAGCCTGATGAGCTCGGCGAT
     GACCCGTAACGCCCGGCTCTGGCACTCGAGCAGAAGGTCCTCGGACTACTCGAGCCGCTA

9061 GGTGGCGCGCACCTCGCGCTCGAAATCCCCGGGGGCCTCCTCTTCTTCCTCTTCTTCCAT
                                  3'-Q-GGAGGAGAAGGAGAAGAAGAAGGTA-R
     CCACCGCGCGTGGAGCGCGAGCTTTAGGGGCCCCCGGAGGAGAAGAAGGAGAAGAAGGTA

9121 GACGACCTCTTCTTCTATTTCTTCCTCTGGGGCGGTGGTGGTGGCGGGGCCCGACGACG
     CTGCTGGAGAAGAAGATAAAGAAGGAGACCCCCGCCACCACCACCGCCCCGGGCTGCTGC

9181 ACGGCGACGCACCGGGAGACGGTCGACGAAGCGCTCGATCATCTCCCCGCGGCGGCGACG
     TGCCGCTGCGTGGCCCTCTGCCAGCTGCTTCGCGAGCTAGTAGAGGGGCGCCGCCGCTGC
```

Quantum Exchange TFOs:

A novel method of monitoring the formation of target amplicons is presented herein.

In this example, a Fluorescein labeled forward primer Adenovirus XCR FOR-FAM is excited with blue light. The Energy of the excited Fluorescein (FAM-T) is transferred to the Nearby (Resorufin-T) on the TFOwave1, which transfers it's energy to the ▓▓▓▓ on TFOwave2, and then finally to the ▓▓▓▓ on the Adenovirus XCR REV-RED. Depending on the availability of naturally occurring TFRs within the amplicon and the length of the amplicon one or more QETFOs may be included in the reaction.

(SEQ ID NO: 50)
Adenovirus XCR FORWARD-FAM: CGTGAGCTCGTCTTCCAGGAGCC(FAM-T)GAT (SEQ ID NO: 51)
Adenovirus XCR REVERSE-RED: GTCTCCCGGTGCG(Cy5-T)CGCCGT (SEQ ID NO: 59)
TFOwave1: 3'-GGAGGAGAAGGAGAAGAAGAAGG(resorufin-T)A-mgb-F (SEQ ID NO: 60)
TFOwave2: 3'-GGAGAAGAAGA(NFAM-T)AAAGAAGGAGA-5'

(SEQ ID NO: 52)
```
9001 CTGGGCATTGCGGGCCGAGACCGTGAGCTCGTCTTCCAGGAGCCTGATGAGCTCGGCGAT
     GACCCGTAACGCCCGGCTCTGGCACTCGAGCAGAAGGTCCTCGGACTACTCGAGCCGCTA

9061 GGTGGCGCGCACCTCGCGCTCGAAATCCCCGGGGGCCTCCTCTTCTTCCTCTTCTTCCAT
                               3'-GGAGGAGAAGGAGAAGAAGAAGG(resorufin-T)A-5'
     CCACCGCGCGTGGAGCGCGAGCTTTAGGGGCCCCCGGAGGAGAAGAAGGAGAAGAAGGTA 9121 GACGACCTCTTCTTCTATTTCTTCCTCTGGGGCGGTGGTGGTGGCGGGGCCCGACGACG
          3'-GGAGAAGAAGA(NFAM-T)AAAGAAGGAGA-5'
     CTGCTGGAGAAGAAGATAAAGAAGGAGACCCCCGCCACCACCACCGCCCCGGGCTGCTGC 9181 ACGGCGACGCACCGGGAGACGGTCGACGAAGCGCTCGATCATCTCCCCGCGGCGGCGACG
     TGCCGC(T-Cy5)GCCGTGGCCCTCTGCCAGCTGCTTCGCGAGCTAGTAGAGGGGCGCCGCCGCTGC
```

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A method of detecting a target nucleic acid sequence, comprising:
    a) providing
        i) a downstream oligonucleotide probe, comprising at least 10 base pairs, having a sequence that is complementary to a first sequence of a target oligonucleotide and that has a cleavable sequence, and
        ii) an upstream oligonucleotide primer, comprising at least 10 base pairs, having a sequence that is complementary to a second sequence of the target oligonucleotide and that has an initial nucleic acid polymerase binding site, and
        iii) a downstream oligonucleotide primer, wherein the downstream oligonucleotide probe is configured for a polymerase to cleave mononucleotides or small oligonucleotides at its 5' end, wherein the Tm of the downstream oligonucleotide probe, the Tm of the downstream oligonucleotide primer, and the Tm of the upstream oligonucleotide primer are each within about 15° C. of the target nucleic acid Tm, and wherein the downstream oligonucleotide primer and the upstream oligonucleotide primer are designed to allow thermal cycling to be conducted within a 15° C. temperature range;
    b) denaturing DNA having the target sequence;
    c) hybridizing the upstream oligonucleotide primer and downstream oligonucleotide probe to the target oligonucleotide;
    d) binding a polymerase to the initial nucleic acid polymerase binding site;
    e) extending the upstream oligonucleotide primer via polymerization with the polymerase toward the downstream oligonucleotide probe;
    f) cleaving nucleotides or small oligonucleotides of the downstream oligonucleotide probe; and
    g) detecting a signal resulting from said cleaving, wherein thermal cycling is conducted at least in part within said 15° C. temperature range.

2. The method of claim 1, wherein the downstream oligonucleotide probe includes a cleavable sequence that is cleaved by polymerization-independent cleavage by a polymerase that binds with the initial nucleic acid polymerase binding site.

3. The method of claim 1, wherein the downstream oligonucleotide probe includes at least one label that is cleaved by nuclease activity.

4. The method of claim 1, wherein the downstream oligonucleotide probe includes a 5' end having a reporter and having a quencher downstream of the reporter.

5. The method of claim 1, wherein the upstream oligonucleotide primer and the downstream oligonucleotide probe are hybridized to the target oligonucleotide.

6. The method of claim 1, wherein the downstream oligonucleotide probe and the upstream oligonucleotide primer anneal to the target oligonucleotide at a sufficiently close nucleotide distance for a nucleic acid polymerase to contact the 5' end of the downstream oligonucleotide probe when binding to the initial nucleic acid polymerase binding site of the upstream oligonucleotide primer.

7. The method of claim 1, wherein the upstream oligonucleotide primer and the downstream oligonucleotide probe are cooperatively configured for the downstream oligonucleotide probe to be cleaved by polymerization-independent cleavage by a polymerase that binds with the initial nucleic acid polymerase binding site of the upstream oligonucleotide primer.

8. The method of claim 1, wherein the downstream oligonucleotide probe and the upstream oligonucleotide primer anneal to the target oligonucleotide at a sufficiently far nucleotide distance for a nucleic acid polymerase to not contact a 5' end of the downstream oligonucleotide probe when the nucleic acid polymerase binds to the initial nucleic acid polymerase binding site of the upstream oligonucleotide primer.

9. The method of claim 1, wherein the upstream oligonucleotide primer and the downstream oligonucleotide probe are cooperatively configured for the downstream oligonucleotide probe to be cleaved by polymerization-dependent cleavage by a polymerase after polymerization.

10. The method of claim 1, wherein the downstream oligonucleotide probe includes an upstream label and a downstream label.

11. The method of claim 1, wherein the downstream oligonucleotide probe comprises a fluorescent dye and quencher located interchangeably on the 5' or 3' end of said probe, such that when the probe is in solution the signal from the fluorescent dye is suppressed by the quencher.

12. The method of claim 1, wherein the downstream oligonucleotide probe comprises a fluorescent dye and quencher located interchangeably on the 5' or 3' end of said probe, such that when binding of the upstream oligonucleotide primer and downstream oligonucleotide probe to the target oligonucleotide occurs, along with the binding of a polymerase to the initial nucleic acid polymerase binding site, the polymerase will cleave either the fluorescent label or the quencher of the downstream oligonucleotide probe.

13. The method of claim 1, wherein one of the upstream oligonucleotide primer or downstream oligonucleotide probe include a bathophenanthroline-RU II complex as a label, and the other of the upstream oligonucleotide primer or downstream oligonucleotide probe includes an energy donor molecule.

14. The method of claim 1, wherein the downstream oligonucleotide probe is a hybrid hairpin/cleaved probe.

15. The method of claim 1, wherein the downstream oligonucleotide probe comprises at least 50 base pairs having a sequence that is complementary to a first sequence of a target oligonucleotide and that has a cleavable sequence, and
   wherein the upstream oligonucleotide primer comprises at least 50 base pairs having a sequence that is complementary to a second sequence of the target oligonucleotide and that has an initial nucleic acid polymerase binding site.

* * * * *